(12) United States Patent
Hasenkam et al.

(10) Patent No.: US 8,591,576 B2
(45) Date of Patent: Nov. 26, 2013

(54) METHOD FOR ALTERING THE GEOMETRY OF THE HEART

(75) Inventors: John Michael Hasenkam, Irvine, CA (US); Morten Smerup, Hojbjerg (DK); Sten Lyager Nielsen, Viby J (DK)

(73) Assignee: Edwards Lifesciences AG, Nyon (CH)

( * ) Notice: Subject to any disclaimer, the term of this patent is extended or adjusted under 35 U.S.C. 154(b) by 101 days.

(21) Appl. No.: 13/396,498

(22) Filed: Feb. 14, 2012

(65) Prior Publication Data

US 2012/0143323 A1 Jun. 7, 2012

Related U.S. Application Data

(63) Continuation of application No. 12/300,786, filed as application No. PCT/DK2007/050058 on May 15, 2007, now Pat. No. 8,142,495.

(60) Provisional application No. 60/809,383, filed on May 31, 2006.

(30) Foreign Application Priority Data

May 15, 2006 (DK) .................................. 2006 00684

(51) Int. Cl.
 *A61F 2/24* (2006.01)
(52) U.S. Cl.
 USPC .......................... 623/2.37; 623/2.36; 128/898
(58) Field of Classification Search
 CPC .......... A61F 2/2451; A61F 2/24; A61F 2/448
 USPC ................ 623/2.36–2.42, 2.1–2.19; 128/898; 606/108
 See application file for complete search history.

(56) References Cited

U.S. PATENT DOCUMENTS

| 3,656,185 A | 4/1972 | Carpentier |
| 4,042,979 A | 8/1977 | Angell |
| 4,055,861 A | 11/1977 | Carpentier et al. |

(Continued)

FOREIGN PATENT DOCUMENTS

| DE | 36 14 292 C1 | 11/1987 |
| DE | 42 34 127 A1 | 5/1994 |

(Continued)

OTHER PUBLICATIONS

Adams, David, et al., "Large Annuloplasty Rings Facilitate Mitral Valve Repair in Barlow's Disease," Society of Thoracic Surgeons 42.sup.nd Annual Meeting, Jan. 30-Feb. 1, 2006.

(Continued)

*Primary Examiner* — Thomas Sweet
*Assistant Examiner* — Jason-Dennis Stewart
(74) *Attorney, Agent, or Firm* — AnnaMarie Kaiser

(57) ABSTRACT

A system (1) for altering the geometry of a heart (100), comprising an annuloplasty ring; a set of elongate annulus-papillary tension members (21, 22, 23, 24), adapted for forming a link between said ring (10) and a papillary muscle, and a first set of papillary anchors (30) for connecting each of the tension members (21, 22, 23, 24) to the papillary muscle; and where said annuloplasty ring (10) has at least one aperture (12, 13); where each of said annulus-papillary tension members (21, 22, 23, 24) are extendable through said ring (10) through said apertures (11, 12, 13), and through an atrium to an exterior side of said atrium, such that the distance of each link between the annulus and the muscles is adjustable from a position exterior to the heart while the heart is beating.

21 Claims, 20 Drawing Sheets

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,261,342 A | 4/1981 | Aranguren Duo |
| 4,275,469 A | 6/1981 | Gabbay |
| 4,290,151 A | 9/1981 | Massana |
| 4,602,911 A | 7/1986 | Ahmadi et al. |
| 4,790,844 A | 12/1988 | Ovil |
| 4,917,097 A | 4/1990 | Proudian et al. |
| 4,960,424 A | 10/1990 | Grooters |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,480,424 A | 1/1996 | Cox |
| 5,496,336 A | 3/1996 | Cosgrove et al. |
| 5,533,515 A | 7/1996 | Coller et al. |
| 5,554,184 A | 9/1996 | Machiraju |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,067 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,957,977 A | 9/1999 | Melvin |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,074,417 A | 6/2000 | Peredo |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,368,348 B1 | 4/2002 | Gabbay |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,629,534 B1 | 10/2003 | St. Goar et al. |
| 6,660,260 B1 | 12/2003 | Rajamannan |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 6,997,950 B2 | 2/2006 | Chawla |
| 7,037,334 B1 | 5/2006 | Hlavka et al. |
| 7,066,954 B2 | 6/2006 | Ryan et al. |
| 7,087,079 B2 | 8/2006 | Navia et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,455,690 B2 | 11/2008 | Cartledge et al. |
| 7,527,647 B2 | 5/2009 | Spence |
| 7,927,370 B2 | 4/2011 | Webler et al. |
| 7,942,928 B2 | 5/2011 | Webler et al. |
| 8,142,495 B2 | 3/2012 | Hasenkam et al. |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2003/0130731 A1 | 7/2003 | Vidlund et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0070999 A1 | 3/2005 | Spence |
| 2005/0075727 A1 | 4/2005 | Wheatley |
| 2005/0131533 A1 | 6/2005 | Alfieri et al. |
| 2005/0137691 A1 | 6/2005 | Salahieh et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |

(56) References Cited

U.S. PATENT DOCUMENTS

| | | |
|---|---|---|
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0149368 A1 | 7/2006 | Spence |
| 2006/0195183 A1 | 8/2006 | Navia et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |

FOREIGN PATENT DOCUMENTS

| | | |
|---|---|---|
| EP | 0338994 A1 | 10/1989 |
| EP | 0595791 A2 | 5/1994 |
| EP | 0860151 A1 | 8/1998 |
| EP | 1034753 A1 | 9/2000 |
| FR | 2708458 A1 | 2/1995 |
| WO | 9119456 A1 | 12/1991 |
| WO | 9503757 | 2/1995 |
| WO | 9640008 A1 | 12/1996 |
| WO | 9741801 A1 | 11/1997 |
| WO | 9742871 A1 | 11/1997 |
| WO | 9806329 A1 | 2/1998 |
| WO | 9911201 A2 | 3/1999 |
| WO | 9930647 A1 | 6/1999 |
| WO | 9951169 A1 | 10/1999 |
| WO | 9965423 A1 | 12/1999 |
| WO | 0032105 A1 | 6/2000 |
| WO | 0119292 A1 | 3/2001 |
| WO | 0126586 A1 | 4/2001 |
| WO | 0147438 A1 | 7/2001 |
| WO | 0187191 A1 | 11/2001 |
| WO | 0203892 A1 | 1/2002 |
| WO | 03020178 A1 | 3/2003 |
| WO | 03041617 A1 | 5/2003 |
| WO | 03053289 A1 | 7/2003 |
| WO | 03105670 A2 | 12/2003 |
| WO | 2004/004607 A1 | 1/2004 |
| WO | 2005/004753 A1 | 1/2005 |
| WO | 2005/034813 A2 | 4/2005 |
| WO | 2005/082278 A2 | 9/2005 |
| WO | 2005/110290 A1 | 11/2005 |
| WO | 2006/041877 A2 | 4/2006 |
| WO | 2006/133186 A2 | 12/2006 |
| WO | 2007-050506 A1 | 5/2007 |
| WO | 2007/100408 A2 | 9/2007 |
| WO | 2007/131513 A1 | 11/2007 |
| WO | 2008/058940 A1 | 5/2008 |
| WO | 2008/063537 A2 | 5/2008 |
| WO | 2008/094469 A2 | 8/2008 |
| WO | 2008/098226 A1 | 8/2008 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Carpentier, et al. "The 'Physio-Ring': An Advanced Concept in Mitral Valve Annuloplasty," Society of Thoracic Surgeons 31.sup.st Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Cochran, et al., Effect of Papillary Muscle Position on Mitral Valve Function: Relationship to Homografts, The Society of Thoracic Surgeons, pp. 5155-5161, 1998.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000, yr. 2000.

Frank Langer, MD, "Subvalvular Repair—The Key to Repairing Ischemic Mitral Regurgitation?" Circulation, Aug. 30, 2005, 112[suppl I], pp. 383-389.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Kasegawa, et al., Mitral Valve Repair for Anterior Leaflet Prolapse With Expanded Polytetrafluoroethylene Sutures, The Society of Thoracic Surgeons, 2006; 81:1625-31.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al., Effect of Annular Shape on Leaflet Curvature in Reducing Mitral Leaflet, American Heart Association, Circulation 200; pp. 106-711, Jul. 2002.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Techniques for 3D Quantitative Echocardiography, University of Washington Cardiovascular Research & Training Center Cardiac Imaging Research Lab, pp. 1-5, Oct. 2003.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association . COPYRGT.2005; ISSN: 1524-4539.

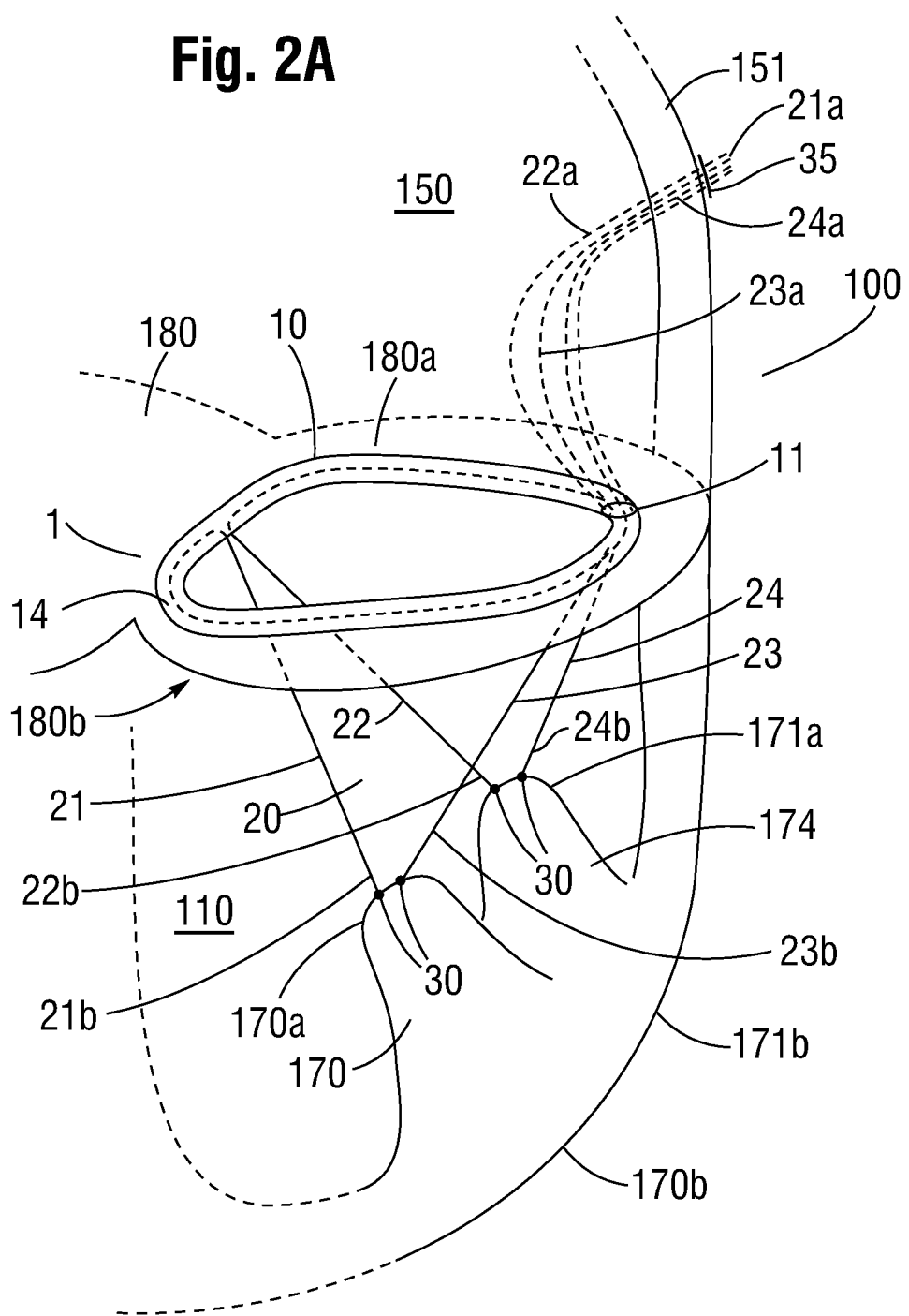

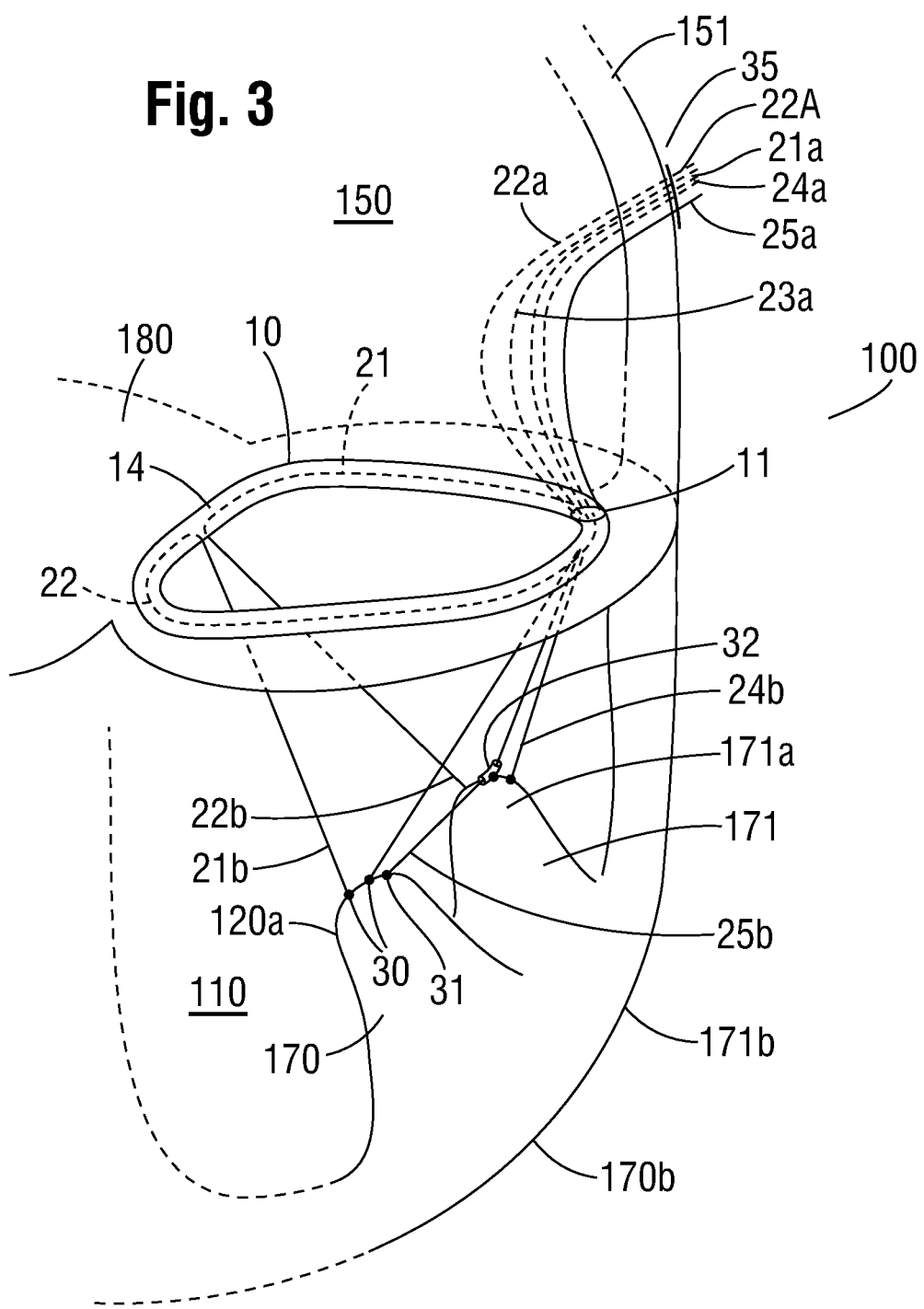

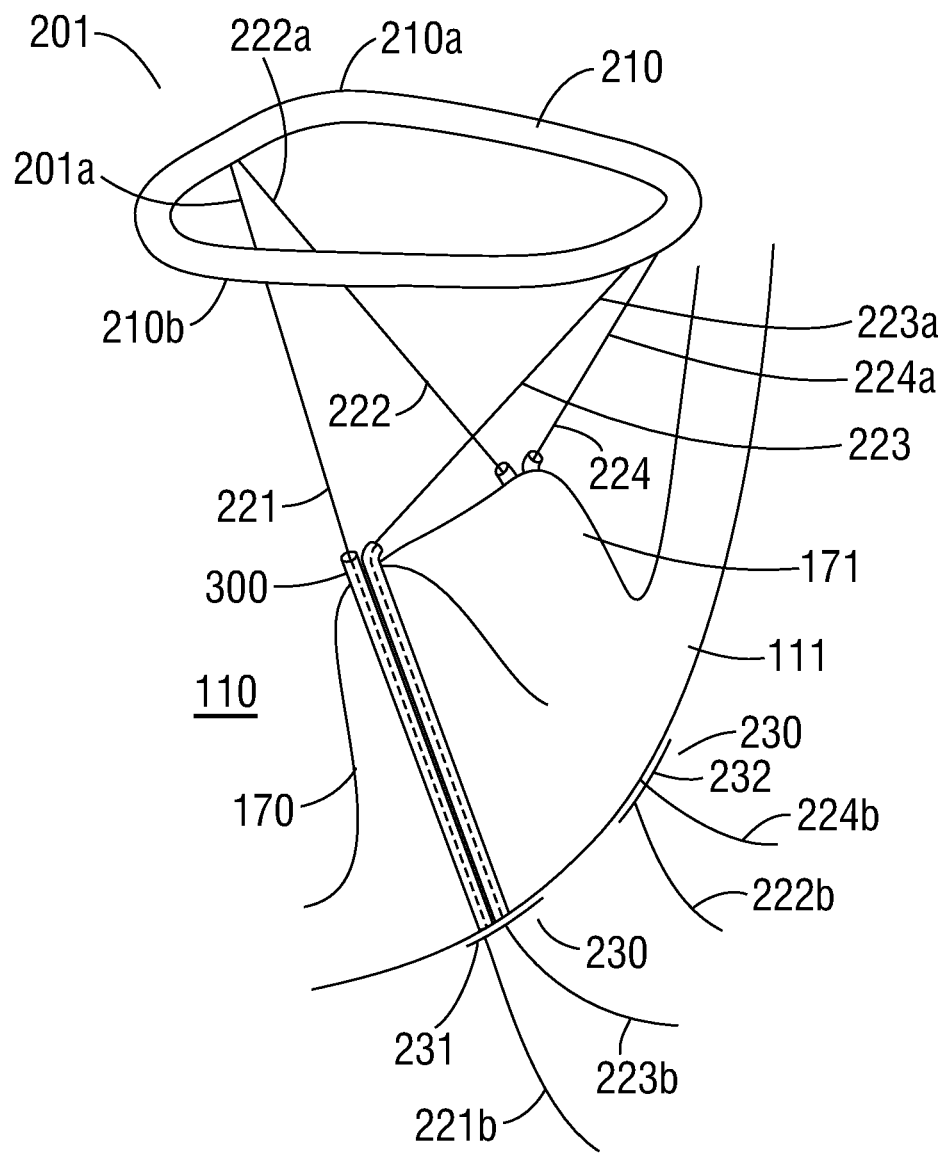

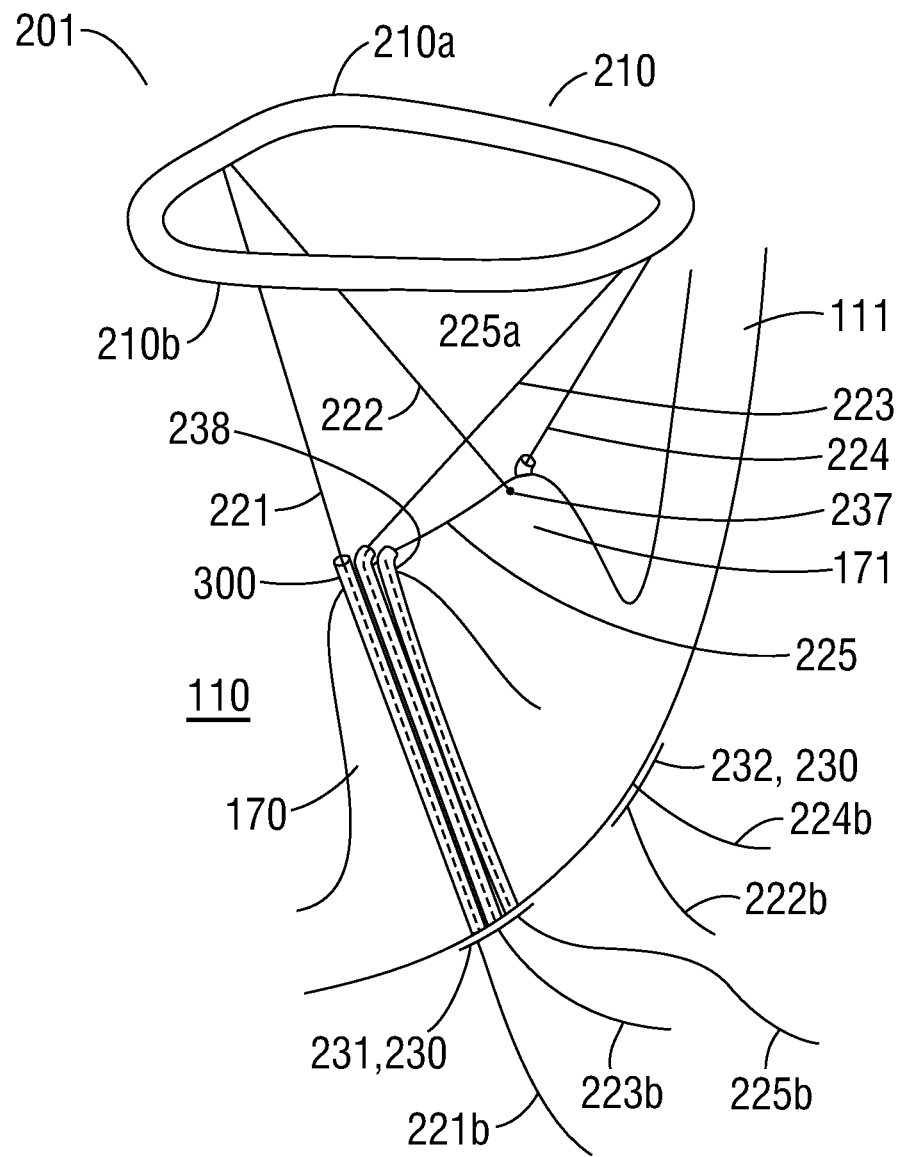

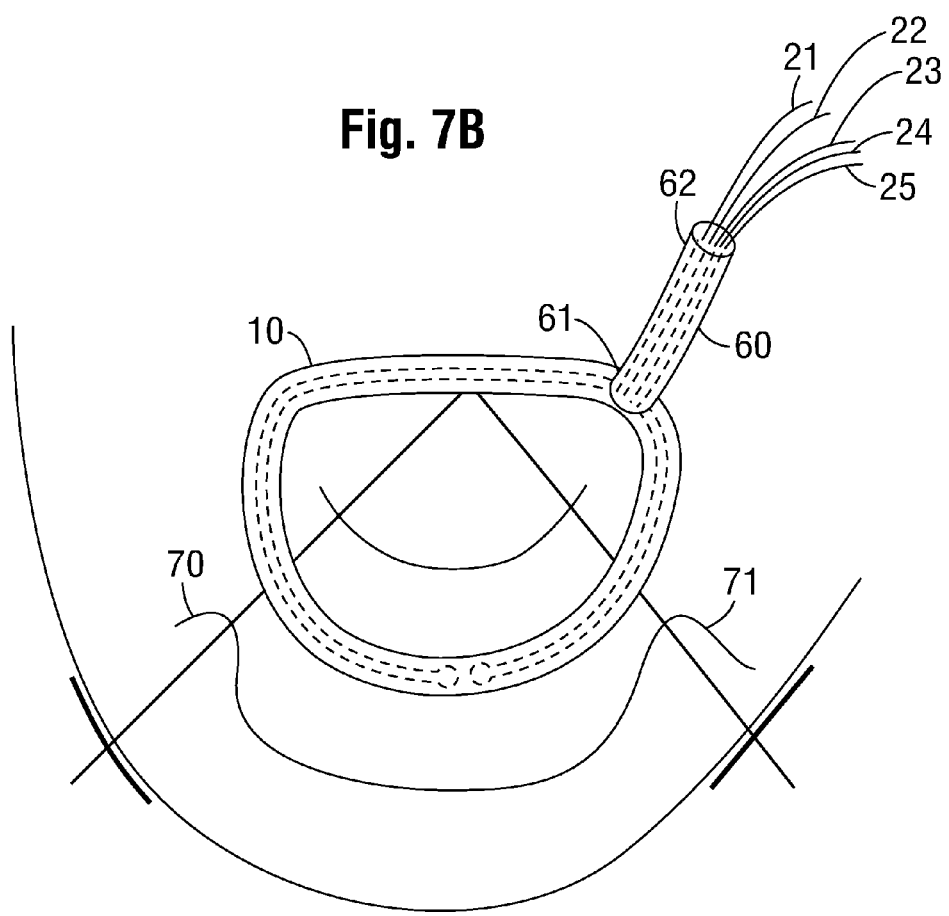

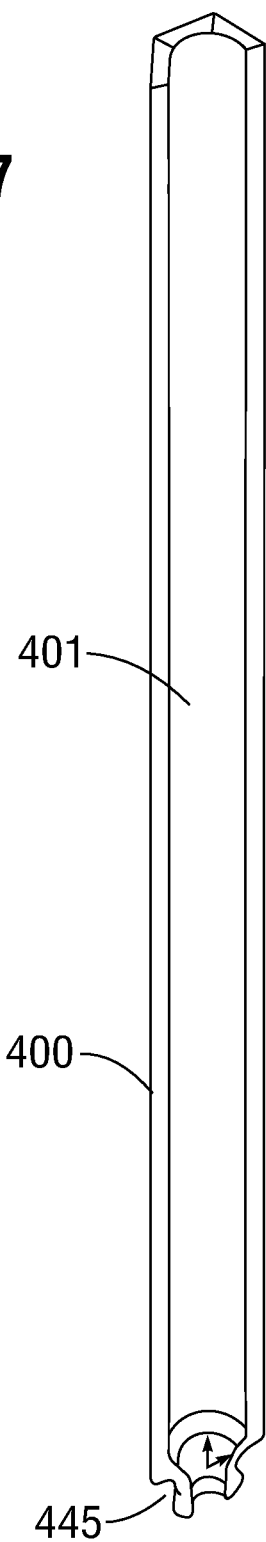

METHOD FOR ALTERING THE GEOMETRY OF THE HEART

RELATED APPLICATIONS

The present application is a continuation of U.S. application Ser. No. 12/300,786, filed Jun. 5, 2009, which is a U.S. National Stage of PCT International Application No. PCT/DK2007/050058, filed May 15, 2007 designating the United States and published in English, which claims the benefit of priority from Danish Patent Application No. PA 2006 00684, filed May 15, 2006, and under 35 U.S.C. 119 from U.S. Provisional No. 60/809,383, filed May 31, 2006. The disclosures of the above-referenced applications are hereby expressly incorporated by reference in their entireties.

FIELD OF THE INVENTION

The present invention concerns systems and methods for altering the geometry of a heart. More specifically the invention concerns systems and methods comprising a number of tension members adapted for restoring the internal geometry of ischemically or otherwise damaged heart chambers. The systems and methods can furthermore be used to alleviate ischemic or functional mitral regurgitation.

BACKGROUND OF THE INVENTION

Despite advances in pharmacologic and interventional therapy, development of functional ischemic mitral regurgitation (MR) after myocardial infarction remains a fundamental cause of morbidity and mortality, especially in western societies. In the United States approximately two million patients suffer from functional ischemic MR, and the annual number of deaths related to this clinical manifestation of ischemic heart disease is increasing. The underlying mechanism for this condition is primarily a dilatation of the left ventricular chamber, which leads to displacement of the papillary muscles. Displacement of these cardiac muscular prominences hamper correct closure of the mitral valve during the ventricular systole and therefore the valve becomes insufficient.

Standard surgical therapy for functional ischemic MR at the time of coronary revascularization (coronary bypass surgery) involves the implantation of a mitral annuloplasty ring, designed to restore coaptation by correcting the posterior annular dilatation common in these patients. Although this can be effective in some patients, results have been variable, and persistent or recurrent MR due to progressive ventricular dilatation and papillary muscle displacement has been reported in at least 20% of the patients.

In order to restore the original left ventricular configuration several attempts to restore left ventricular shape and function have been exhibited in form of "Coapsys" device, Dor procedure and Acorn device. However, these principles of treatment are fairly primitive or crude, and therefore do not match the complex anatomy, physiology and mechanics related to the functionality of the mitral valve. Also known in the art are a number of devices for altering the geometry of the heart, e.g. as disclosed in WO 2005/082278, describing a semi-circular papillary muscle and annulus bands for modifying the alignment of papillary muscles, a mitral valve annulus and/or a tricuspid valve annulus. Also disclosed are methods to effect the alignment and a sizing device that can be used for such alignment.

The set of devices disclosed in WO 2005/082278 allows the surgeon to alter, i.e. restore the geometry of the heart. However, all of the above mentioned procedures—including the one disclosed in WO 2005/082278—require that the heart is stopped during the insertion and adjustment of the devices. In this condition the geometry of the heart is very dissimilar to that of the functioning heart since it collapses upon evacuation of blood from its chambers. The adjustment of the functional constituents of the devices—the tension members—during heart arrest may therefore be inaccurate, and the geometry of the device and the heart cannot be altered once the heart is surgically closed, and cardiac function is resumed after the insertion of the device. Therefore, it is difficult to assess if the desired geometry is restored at this stage—before the heart function is resumed.

Consequently, the lengths of the devices must be very thoroughly assessed prior to the surgery procedure. Since the heart with its valves and subvalvular apparatus is a complex dynamic system, where the individual components move in an interdependent and coordinated manner, such an assessment may be extremely difficult. Alternatively, a certain margin of error must be accepted.

There is thus a need for a system and a method for altering the geometry of a heart that allows the altering or at least an adjustment of the geometry of the heart to take place when the heart is beating.

OBJECT OF THE INVENTION

It is an object of the present invention to provide a system for altering the geometry of the heart that exerts a more advanced approach to treating ischemic mitral valve disease.

It is a further an object of the invention to provide a system for altering the geometry of the heart, which both enables reduction and stabilization of the mitral annulus and entails remodeling of the left or right ventricle.

It is a further an object of the invention to provide a system for altering the geometry of the heart, which allows repositioning of the papillary muscles and at the same time supports the left ventricular myocardium and prevents further dilatation of the left heart chambers.

It is a further object of the invention to provide a system for altering the geometry of the heart, which allows for easy insertion into and placement in the heart.

It is a further object of the invention to provide a system for altering the geometry of the heart, which allows adjustment of the system and thereby the geometry of the heart on the beating heart.

It is a further object of the invention to provide a system for altering the geometry of the heart, which constitutes an alternative to existing devices for altering the geometry of the heart.

SUMMARY OF THE INVENTION

The object of the invention is accomplished by a first aspect of a system for altering the geometry of a heart comprising an annuloplasty ring for supporting the geometry of an annulus of the heart, being attachable to said annulus, and having an upper side and a lower side; a set of elongate annulus-papillary tension members each of which tension members are adapted for forming a link between said annuloplasty ring and a papillary muscle of the heart, each of said tension members having a first end and a second end; and a first set of papillary anchors for connecting each of the second ends of said annulus-papillary tension members to said papillary muscle; wherein said annuloplasty ring has at least one aperture located on said lower side and at least one aperture located on said upper side and where each of said annulus-papillary tension members are extendable through said annuloplasty ring through said apertures, and through an atrium of said heart to an exterior side of an exterior wall of said atrium such that the distance of each link between the annulus and the papillary muscles is adjustable from a position exterior to the heart.

Thereby is achieved a system in which the normal geometry of the ventricle can be re-established from the exterior of the heart at the exterior atrium wall. This allows a surgeon to perform the adjustment process of the tension members of the system, not only on the beating heart, but also on the beating heart that is correctly positioned in the thorax. This is due to the orientation of the left atrium in the body of a human. The left atrium is ready accessible when the thorax has been opened.

In an embodiment of the first aspect, the system further comprises an inter-papillary tension member for forming a link between said papillary muscles, said inter-papillary tension member having a first end and a second end; a first inter-papillary anchor for fixing the second end of said inter-papillary tension member to a papillary muscle; and a second inter-papillary anchor through which the first end of said inter-papillary tension member is extendable, said inter-papillary tension member further being extendable through a ventricle of said heart, and through said annuloplasty ring via said apertures and through an atrium of said heart to an exterior side of an exterior wall of said atrium wall of said atrium, such that the distance of the inter-papillary link between the papillary muscles is adjustable from a position exterior to the heart.

Thus the distance between the papillary muscles can also be adjusted from the exterior atrium side on the beating heart.

In a further aspect of the invention the object is achieved by a system as stated in the claims. More particularly a system for altering the geometry of the heart is achieved in which the ventricle geometry may be adjusted on a beating heart, from a position outside the heart, and through the ventricle.

The object of the invention may further be achieved by an annuloplasty ring for supporting the geometry of an annulus of the heart, being attachable to said annulus, and having an upper side and a lower side, where said annuloplasty ring has at least one aperture located on said lower side and at least one aperture located on said upper side and wherein a set tension members are extendable through said annuloplasty ring through said apertures.

Such an annuloplasty ring may be used with any of the embodiments of the first aspect of the invention as cited above.

The annuloplasty ring may further comprise a channel formed along the circumference of the annuloplasty ring, said channel connecting said upper aperture located on said upper side to at least one aperture located on said lower side, where the upper and lower apertures are positioned diametrically across from each other on the circumference of the annuloplasty ring.

The annuloplasty ring may further comprise a tension member hub having a set of upper apertures communicating with a set of lower apertures via a set of channels, and where a set of tension members may be locked to the annuloplasty ring at said hub.

The annuloplasty ring hub may comprise a locking part mounted in a through hole of the hub for locking/fixating tension members, and fastening means for locking/fixating the locking part to the though hole of the hub.

The invention further regards a system according to the first aspect of the invention that further comprises a tightening tool for fasting the fastening member in order for locking/fixating tension members.

Further understanding of the nature and advantages of the invention will become apparent by reference to the remaining portions of the specification and drawings.

BRIEF DESCRIPTION OF THE DRAWINGS

FIG. 2A shows, in schematic form, a perspective view of a system for altering the geometry of a heart according to a first aspect of the invention, when situated in a heart;

FIG. 3 shows, in schematic form, a perspective view of the system for altering the geometry of a heart according to an embodiment of the first aspect of the invention, when situated in a heart;

FIG. 4 shows, in schematic form, a perspective view of a system for altering the geometry of a heart according to a second aspect of the invention, when situated in a heart;

FIG. 5 shows, in schematic form, a perspective view of a system for altering the geometry of a heart according to an embodiment of the latter (second) aspect of the invention, when situated in a heart;

FIG. 7B shows a top view of the system shown in FIG. 7A;

FIG. 17 shows a section through a tightening tool for tightening/locking/fastening tension members at an annuloplasty ring of a system for altering the geometry of a heart.

DESCRIPTION OF THE PREFERRED EMBODIMENTS

Figure 1A:
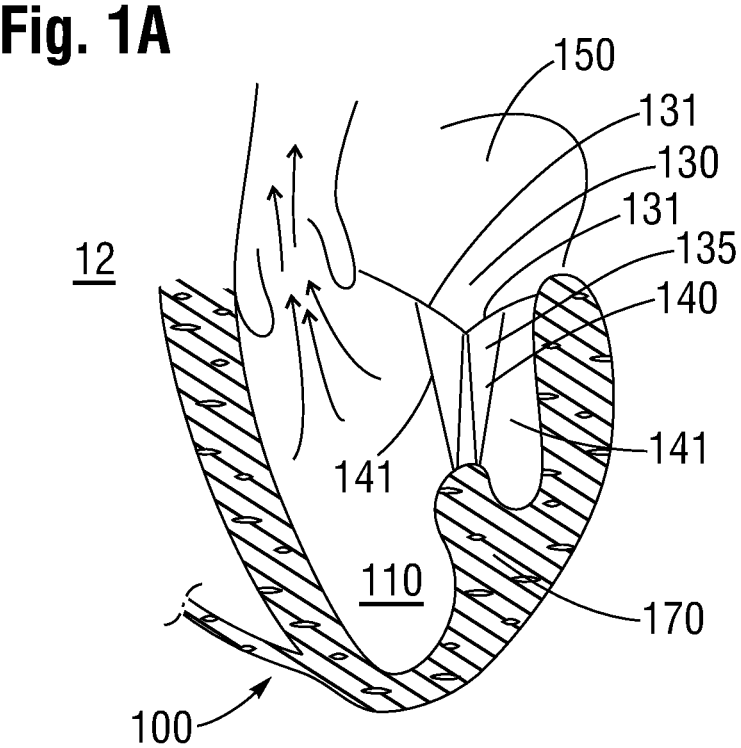
FIGS. 1A-C, in schematic form, show a section through a portion of a heart, in three conditions.

Initially and in order to describe the present invention, an example of a physical condition of a heart 100 that can be remedied using the system and the method of the present invention is briefly described with reference to FIGS. 1A-C. FIG. 1A shows a section through a portion of a normally functioning heart 100. More particularly, FIG. 1A shows in schematic form a long-axis section through a left ventricle 110 of a normal heart 100 during systole. The aortic valve 120 is open (the arrows in the vicinity of the valve 120 indicating the flow of blood), while the mitral valve 130 is closed. The mitral valve 130 has two leaflets 131. Primary and secondary chordae 140, 141 ensures that the two leaflets 131 of the mitral valve 130 interact over a broad, so-called coaption area 135 to ensure a tight mitral valve 130 function, thus preventing blood from re-entering the left atrium 150 (mitral regurgitation 136, see FIG. 1B). In the figure (FIG. 1A) one papillary muscle 170 is also shown. The chordae 140, 141 and the papillary muscles 170 are also referred to as the subvalvular apparatus.

Figure 1B:
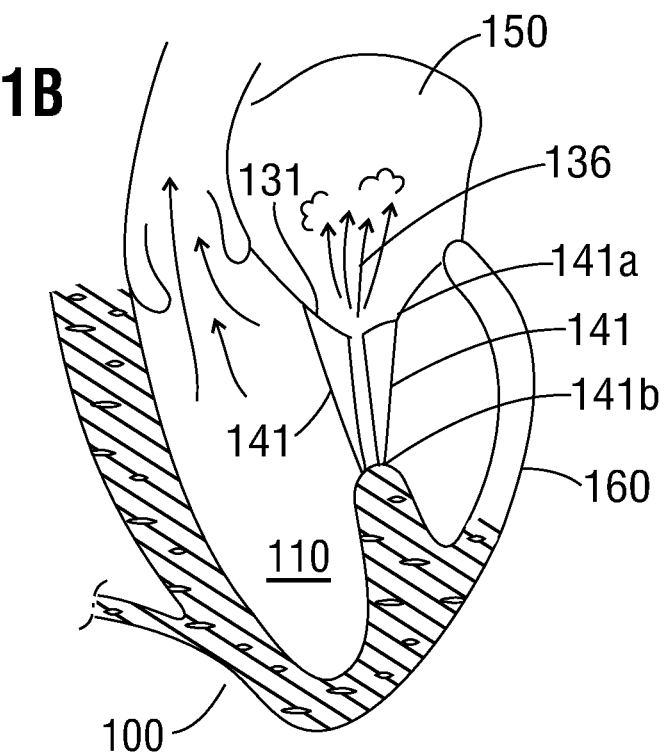

In FIG. 1B a section similar to the one shown in FIG. 2A is shown, where a portion of the posterior left ventricular myocardial wall has formed scar tissue 160, e.g. following coronary atherosclerosis and thrombosis. As a consequence, the papillary muscles 170 are displaced: down, out, and away from each other (in this view only a single papillary muscle is shown). The leaflets 131 of the mitral valve 130, thereby, are drawn down and into the ventricle via the secondary chordae 141—a condition known as tethering. Consequently, the mitral valve 130 leaks blood to the atrium 150 during systole, as indicated by the arrows 136, i.e. the phenomenon of mitral regurgitation is experienced. Further, as a consequence of this condition the left ventricle 110 is enlarged/dilated. Thus, a geometrical analysis of this condition shows that the angle between the leaflets 131 of the mitral valve 130 and the secondary chordae 141 has diminished due to the increased distance between the affixture 141a of the secondary chordae 141 to the mitral valve leaflet 131 and the origin 141b of the secondary 141 chordae on the papillary muscle 170.

Figure 1C:
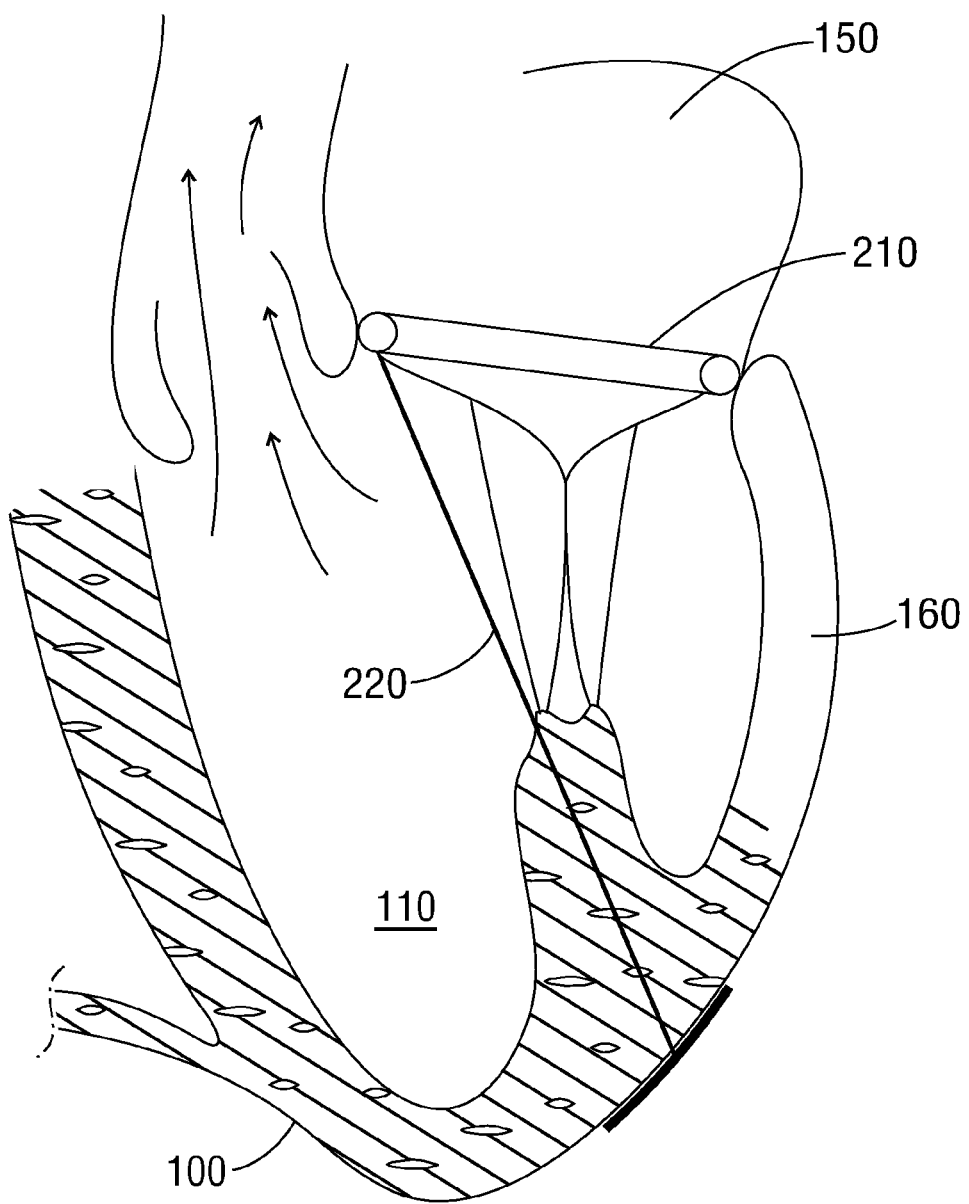

In FIG. 1C it is shown how the normal geometry of the heart can be re-established when a system 1 according to an embodiment of a second aspect of the invention (to described in further detail below) is positioned in the heart 100. The system comprises an annuloplasty ring 210 and a tension and anchoring system 220, which allows adjustment of a set of tension members of the anchoring system 220 from the exterior side of the heart wall on the beating heart, such that an improved correction of the geometry of the heart 100 can be accomplished.

Here and in the following, the invention is explained in relation to its use in the left side of the heart. It should, however, be mentioned that the invention applies also to similar conditions of the tricuspid valve (not shown) of the right side of the heart 100, with an adaptation to the three valvular leaflets of this valve.

In the following we will describe a set of aspects and embodiments of the invention. Throughout the following description of embodiments of the invention the same reference numbers are used for like parts, although they may vary slightly in detail.

FIG. 2A represents in a simplified diagram form, an embodiment of a first aspect of a surgical system 1 for altering the geometry of the heart 100, in the form of a system 1 adapted to restoring the normal geometry of the mitral valve 130 subvalvular apparatus 140, 141, 170 and the geometry of the left ventricle 110.

The system 1 according to the first aspect of the invention allows adjustment of tension member through the atrium 150 of the heart.

The system 1 according to the embodiment of the invention shown in FIG. 2A includes a complete, substantially rigid, hollow mitral annuloplasty ring 10 and a tension and anchoring system 20 adapted to align the papillary muscles 170 with the annulus 180 and to align the wall of the left ventricle with respect to the mitral valve 130 in order to eliminate ischemic/functional mitral regurgitation 136 (see explanation above).

The tension system comprises a set of tension members 21, 22, 23, 24, e.g. in the form of strings or sutures. Each of the tension members comprises a first end 21a, 22a, 23a, 24a and a second end 21b, 22b, 23b, 24b, respectively. The first ends 21a, 22a, 23a, 24a are intended to be led to a position at the exterior of the heart for adjustment of a set of anatomical lengths/distances defining the geometry of the ventricle 110 of the heart 100. The second ends 21b, 22b, 23b, 24b are intended for fixture to a position on or through the papillary muscles 170.

The annuloplasty ring 10 is hollow forming at least one circumferential channel 14 to allow passage of a potion of a set of the tension members 21, 22, 23, 24 (as indicated by the dotted line in the ring 10 shown in FIG. 2A) that constitute part of the tension system 20.

The annuloplasty ring 10 is attachable to the annulus 180 of the heart 100. Its rigidity will—when attached to the annulus—support the geometry of the annulus 180. The tension members 21, 22, 23, 24 may run in a single or in multiple separate internal compartments or circumferential channels formed along portions of the perimeter of the annuloplasty ring 10. One end 21a, 22a, 23a, 24a of each tension member extending from one side (the upper side 10a) and another end 21b, 22b, 23b, 24b extending from the opposite side (the lower side 10b) of the annuloplasty ring 10.

Figure 2B:
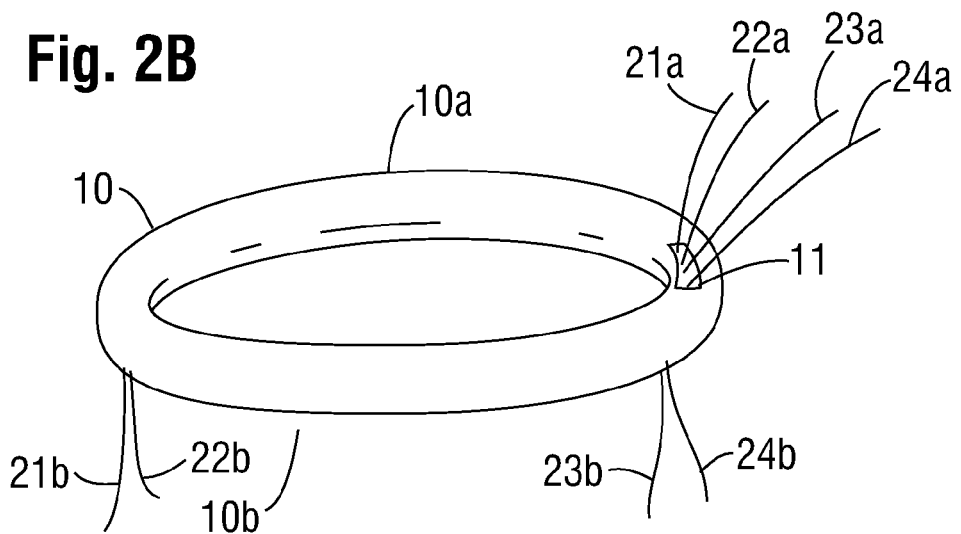
FIGS. 2B-E show, in schematic form, a perspective view of components of the system shown in FIG. 2A.

These compartment(s) communicate with an upper (atrial) side 10a of the ring 10 via a single aperture 11 in the annuloplasty ring 10 as shown in FIG. 2B, through which aperture the first ends 21a, 22a, 23a, 24a, of said tension members extend to the atrium side 10a of the annuloplasty ring 10. The first ends 21a, 22a, 23a, 24a are extendable to the exterior wall 151 of the atrium 150 of the heart 100 (see below), and thus must be adapted to a suitable length for this purpose. The singular aperture 11 may in alternative embodiments be substituted with a number of individual apertures (not shown) for each tension member 21, 22, 23, 24 provided these apertures are situated close to each other on the ring, i.e. within a 30° angle of the ring 10.

Figure 2C:
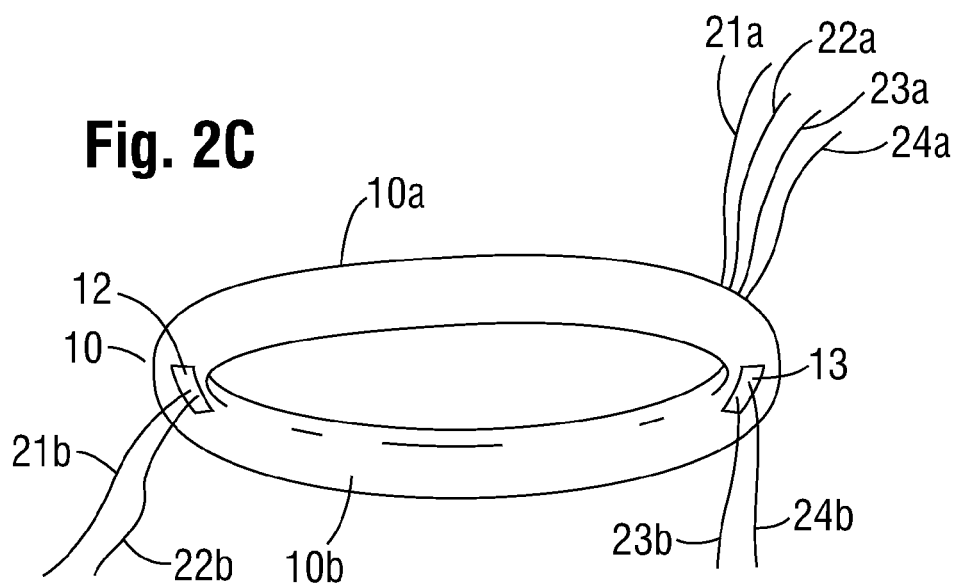
Figure 2D:
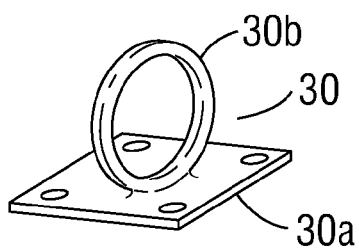
Figure 2E:
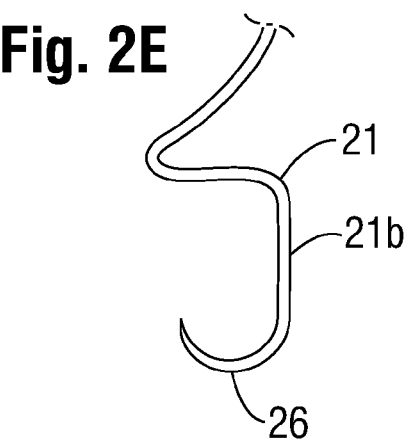

The internal compartment(s) of the ring 10 also communicate with the lower (ventricular) side 10b of the ring 10 via a set of preferably two apertures 12, 13 formed in the lower surface 10b of the annuloplasty ring 10 as shown in FIG. 2C. Through these apertures 12, 13, the second ends 21b, 22b, 23b, 24b, of said tension members extend to the ventricular side 10a of the annuloplasty ring 10. The second ends 21b, 22b, 23b, 24b are adapted to be extendable to the papillary muscle of the left ventricle (see below), and thus must be adapted to a suitable length for this purpose.

The lower side 10b apertures 12, 13 are preferably situated diametrically across from each other. Two tension members 21, 22 extend through one of the lower apertures 12 and two other members 23, 24 are carried through the other of the lower side apertures 13. The above mentioned apertures 11, 12, 13 may be reinforced along the rim of the apertures 12, 12, 13 in order to increase the resistance to wear and tear of tension members being moved/drawn with respect to the apertures. In an embodiment (not shown) the lower (ventricle) side 11b of the annuloplasty ring 10 may be provide with one aperture for each tension member 21, 22, 23, 24.

The system 1 according to the embodiment of the first aspect of the invention shown in FIG. 2A further comprises an exterior heart wall anchor 36 attachable to said first ends 21a, 22a, 23a, 24a, of said tension members 21, 22, 23, 24, for attaching/fixing said first ends 21a, 22a, 23a, 24a, with respect to a position on the exterior dome wall 151 of the atrium 150.

Figure 6A:
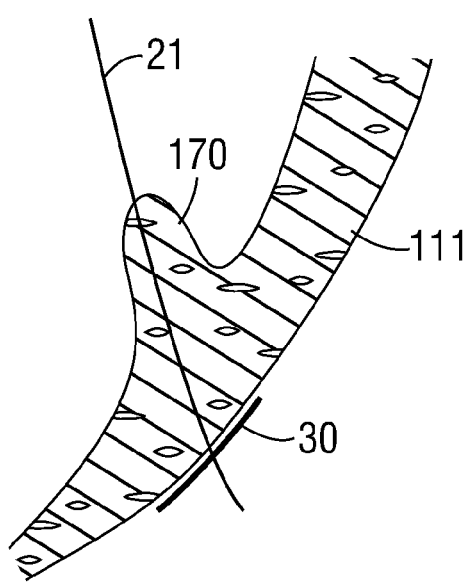
FIGS. 6A-C show different options for anchoring a tension member to a papillary muscle.
Figure 6B:
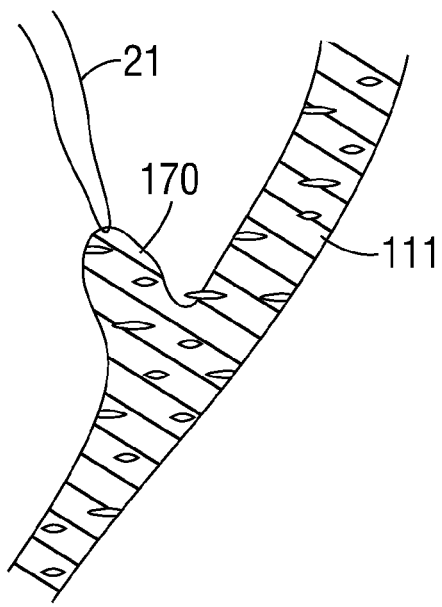
Figure 6C:
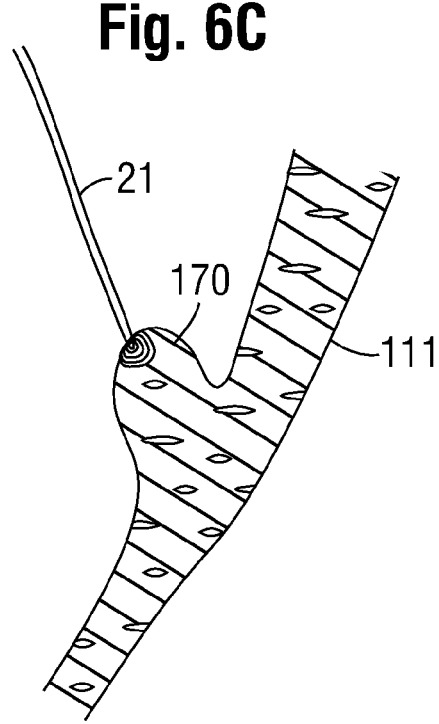

The second ends 21b, 22b, 23b, 24b, of the tension members are attachable/fixable to the tip 170a of the papillary muscle 170, by a first set of papillary anchors 30 of the system 1. These papillary anchors 31, 32, 33, 34 may in their simplest form be sutured fixture points for the second ends 21b, 22b, 23b, 24b of the tension members 21, 22, 23, 24. However, the anchors may also comprise a slap 30a and a loop 30b attached to said slap 30a on one side. On the other side the slap may be provided with means for fixing the anchor to the papillary muscle e.g. apertures for pins, sutures, hooks, screws or an ingrowth enhancing material. Examples of some alternative anchoring options are shown in FIG. 6. In FIG. 6A it is shown how a tension member can be anchored by providing a pad or anchor 30, e.g. in the form of a disc-shaped slap on an exterior surface of a wall 111 of the heart 100. Such an anchor may be provided with a mechanism for securing the tension member in a fixed position with respect to the anchor 30. In a simple form such a mechanism may be a loop or a hole to which a flexible tension member may be tied. However, the mechanism may also comprise means for pinching screwing or otherwise adjustably securing the tension member in fixed position. In FIG. 6B it is shown how a tension member 21 can be anchored to a papillary muscle 170 tip by simple suturing. In FIG. 6C it is shown that the anchoring may be provided by the tension member 21 is secured to a papillary muscle 170 via a slap of flexible material which may itself be sutured onto the tissue. These alternative anchoring options are not only alternatives useful for the first aspect of the invention as described above, but also for the aspects and embodiments described in the following.

Some or all of the anchors 30, 31, 32, 34 may be anchored to other points within the ventricle 11, apart from the papillary tips 170a, 171b, in suitable places on the ventricular wall.

The system 1 thereby provides for adjusting to a desired fixed maximum distance between each of the papillary muscles 170 and a fixed point (at the aperture 12, 13 on the lower side 10b) on the annuloplasty ring 10, and thereby on the annulus (When the annuloplasty ring 10 is attached to the annulus 180.

Thus the geometry of the left ventricle can be altered, i.e. restored partly or fully to its normal geometry, using the device according to the above described embodiments of the first aspect of the invention, in a way described below.

In the following, an alternative embodiment of the first aspect of the invention will be described with reference to FIG. 3. The system 1 according to this embodiment of the invention is generally similar to the one described above, and with the same variation possibilities. However the system 1 in this embodiment further comprises an additional tension member, namely an inter-papillary tension member 25 formed attachable by a second end 25b to one of one papillary muscle tip 170a via a first inter-papillary anchor 31, and an additional second inter-papillary anchor 32. The system 1 is formed with the interpapillary tension member 25 extending through said annuloplasty ring 10. On the upper side 10a of said annuloplasty ring a first end 25 of said inter-papillary tension member 25 preferably extends through said aperture 11, together with tension members 21, 22, 23 and 24 as shown in the figure (FIG. 3). However, it may also extend through a separate aperture (not shown), provided that the aperture is located within the same angle as specified for the tension members 21-24 in the FIG. 2—embodiment described above.

The second end 25b of said inter-papillary tension member 25 preferably extends through the other, lower side 10b of the annuloplasty ring 10, through one of said lower side apertures 12, 13. However, a separate aperture (not shown) may be provided for the inter-papillary tension member 25 on the lower side 10b of the annuloplasty ring 10.

The second end 25b of said inter-papillary tension member 25 is adapted such that the length at least allows an extension of the member 25 from the ring 10 to a first papillary muscle tip 170 and on to the other papillary muscle tip 170a.

Thus the geometry of the left ventricle can be altered, i.e. partly or entirely restored to its normal geometry, using the device according to the above describe embodiments of the first aspect of the invention, in a way described below. In particular, with this embodiment the interpapillary distance may be very easily adjusted.

In the following, and with reference to FIGS. 4 and 5, embodiments according to a second aspect of the invention are described. With the embodiments of the system 201 according to this second aspect of the invention the system may be adjusted from outside of the ventricle 110 portion of a wall 111 of the heart 100.

In the embodiment shown in FIG. 4, the system 201 comprises an annuloplasty ring 210, a set of tension members 220, 221, 222, 223, 224 and a first set of papillary anchors 230 for connecting each said annulus-papillary tension members 221, 222, 223, 224 to either of a set of papillary muscle 170, 171 of a heart 100, or alternatively to other positions on the ventricular wall.

The annuloplasty ring 210 is attachable to an annulus 180 of the heart 100. It has an upper side 210a and a lower side 210b which, when the ring 210 is inserted in the heart 100, is intended to face the atrium 150 and the ventricle 110, respectively.

The set of elongate annulus-papillary tension members 221, 222, 223, 224 are each adapted for forming a link between said annuloplasty ring 210 and a papillary muscle 170, 171 of the heart 100. Each of said tension members 221, 222, 223, 224 has a first end 221a, 222a, 223a, 224a and a second end 2221b, 222b, 223b, 224b. Said first ends 221a, 222a, 223a, 224a are attached fixedly to the annuloplasty ring 210, preferably such that a set of two tension members 221, 222 extend from a first point on the lower side 210b of the annuloplasty ring 210, and another set of two tension members 223, 224 extend from a second point, preferably diametrically opposed to said first point, on said annuloplasty ring 210. However, the tension members may alternatively extend from distinct individual points on the lower side 210b of the annuloplasty ring 210.

Each of the annulus-papillary tension members 221, 222, 223, 224 are configured such as to allow extension of said second ends 221b, 222b, 223b, 224b through a papillary muscle 170, 171 to an exterior side 170b of an exterior wall 111 of a ventricle 110 of a heart 100, to a first set of papillary anchors 230 for connecting each of the first ends 221b, 222b, 223b, 224b of said annulus-papillary tension members 221, 222, 223, 224 to said papillary muscle 170, 171. Alternatively, some or all the tension member 221, 222, 223, 224 second ends 221b, 222b, 223b, 224b may be extended to and through other points on the ventricular wall 111, to be anchored at these points.

The system 201 may be configured such that there is one anchor 230 available for each papillary muscle 170, 171, such that a first set of two tension members 221, 223 can be attached to and adjusted at one anchor 231 and second set of tension member can be attached to a second anchor 232.

The system 201 may further comprise tubular members 300 for providing a channel through the papillary muscle 70, 71 or the ventricular wall 110, the tubular members being adapted for guiding the tension members 221, 222, 223, 224. Thus, the wear and tear on the tissue, through which the tension members 221, 222, 223, 224 is extended during use of the system 201 is minimized. The tubular members may be formed integrally with anchors 230.

Preferably the anchors 230 have means for individually fixing each of the second ends 221b, 222b, 223b, 224b of said annulus-papillary tension members 221, 222, 223, 224, such that the length of each tension member can be adjusted individually.

Thus the geometry of the left ventricle can be altered, i.e. partly or entirely restored to its normal geometry, using the device according to the above describe embodiments of the second aspect of the invention, in a way described below.

In the following, an alternative embodiment of the second aspect of the invention will be described with reference to FIG. 5. The system 201 according to this embodiment of the invention is generally similar to the one described above (with reference to FIG. 4), and with the same variation possibilities as described for that embodiment. However the system 201 in the present embodiment further comprises an additional tension member, namely an inter-papillary tension member 225 for forming a link between the two papillary muscles 170, 171, adjustable from a position exterior to the ventricle wall, upon insertion of the system into the heart 100. The inter-papillary tension member 225 has a first end 225a and a second end 225b.

The system 201 further comprises a third papillary anchor 237 for fixing the first end 225a of said interpapillary tension member 225 to a papillary muscle 171, and fourth papillary anchor 238 through which the second end 225b of said inter-papillary tension member 225 is extendable, the inter-papillary tension member 225 being configured such that the second end 225b can be extended to the exterior side of said ventricle wall 111 to be secured to one of the first set of anchors 30 of the system 1, through a papillary muscle 170 of said heart 100, and in such a way that the distance of the inter-papillary link between the papillary muscles 170, 171 is adjustable from a position exterior to the heart 100.

Preferably, the system 1 is configured such that second end 225b of the interpapillary tension member 225 is fixable to one anchor of said first set of anchors 230, and such that this anchor 230 has means for individually fixing the second end 225b of said inter-papillary tension member 225.

Thus, the geometry of the left ventricle can be altered, i.e. partly or entirely restored to its normal geometry, using the device according to the above describe embodiments of the first aspect of the invention, in a way described below. In particular, with this embodiment the interpapillary distance may be very easily adjusted.

The annuloplasty ring 10, 210 is in either aspect of the invention preferably formed from a biocompatible material. Suitable biocompatible materials are known in the medical industry, and include Dacron®, titanium, silicone, nitinol, polyesters, and denatured biological material.

The tension members 21, 22, 23, 24, 25, 221, 222, 223, 224, 225 in either aspect of the invention, are preferably formed in a biocompatible material. Suitable biocompatible materials known from the medical industry include Dacron, titanium, silicone, nylons, polypropylene, nitinol, polyesters, and denatured biological material.

In the following a set of basic implantation techniques for the system 1 for altering the geometry of a heart 100 is briefly explained in order to reveal new and improved methods for altering the geometry of the heart.

After opening the chest to provide access to the heart, and ceasing the heart function, the mitral valve 130 is exposed using standard surgical techniques, by resecting the heart wall 151 at the atrium 150, and inserting the system 1 according to either of the aspects as outlined above. This initial step of course is common to all aspects of the methods according to the invention as described below.

In a first aspect of a method for altering the geometry of a heart using the system 1 shown and described in relation to FIG. 2, where the annuloplasty ring 10 is attached to the atrial side 180a of the mitral annulus 180, the second ends 21b, 22b, 23b, 24b of the valve/papillary tension members 21, 22, 23, 24 are brought from the atrial 180a, to the ventricular 180b aspect of the annulus 180 by piercing the annulus 180 at positions corresponding to the points of exit of the tension members 21, 22, 23, 24, from the annuloplasty ring 10. This piercing may be provided by a separate surgical tool, or it may be provided by needles/suture needles (26) disposed at the second end of one or more of said tension members, see FIG. 2E. The second ends 21b, 22b, 23b, 24b are secured/fixated to the papillary muscle tips 170a (or a place on the ventricular wall 111) by means of suitable anchors 30 of the system 1 or other fixation means. The annulus-papillary tension members 21, 22, 23, 24 are distributed such that a tension member from each point of exit on the annuloplasty ring 10 is connected to each papillary muscle tip 170a.

Hereafter, the annuloplasty ring 10 is fixated to the atrium side 180a of the annulus 180 e.g. by means of interrupted sutures following standard surgical techniques. As an alternative to the fixating of the second ends 21b, 22b, 23b, 24b of the annulus-papillary tension members 21, 22, 23, 24 to the tips 170a of the papillary muscles 170, they may be passed through the papillary muscles 170 and the left ventricular wall to the epicardial aspect 170b of the papillary muscle base and fixated to an anchor exterior to the heart wall at this position (not shown).

When the annuloplasty ring 10 and the anchoring system has been inserted into and fixed to the correct point of the heart 100, all the first ends 21a, 22a, 23a, 24a of the tension members 21, 22, 23, 24 are exteriorized through the dome 151 of the left atrium 150. Then the heart is surgically closed, its cavities evacuated from air and allowed to fill with blood, and normal heart rhythm is resumed. Under echocardiographic guidance the tension members 21, 22, 23, 24 are adjusted (tightened or loosened relative to each other) to maximize cardiac function and valve competence. Hereafter the tension members 21, 22, 23, 24 are tied in a standard surgical fashion, or tightened in a standard surgical fashion around an anchor 35 such as a special epicardial pad to reduce the local myocardial damage.

In another embodiment of this first aspect of a method according to the invention, using the system 1 shown and described in relation to FIG. 3 a further inter-papillary tension member 25 may be placed in the heart along with the valve-papillary tension members 21, 22, 23, 24. A second end 25b of the inter-papillary tension member 25 is brought through the annulus 150 together with the second ends 21b, 22b, 23b, 24b of valve-papillary tension members 21, 22, 23, 24. An inter-papillary anchor 45 is then fixed to a tip 170a of one of the papillary muscles 170. The ventricular end 25b of the inter-papillary tension member 25 is then connected via the inter-papillary anchor 32 to the tip 170a of the other papillary muscle 170, where it is fixated, by means of suitable anchors or other fixation means. Then the first end of the inter-papillary tension member 25 is exteriorized through the dome 151 of the left atrium 150 together with the first ends 21a, 22a, 23a, 24a of the valve-papillary tension members 21, 22, 23, 24, and adjusted (tightened or loosened relative to each other) to maximize cardiac function and valve competence. Hereafter the tension members 21, 22, 23, 24, 25 are tied in a standard surgical fashion, or tightened in a standard surgical fashion around an anchor 35 such as a special epicardial pad to reduce the local myocardial damage on the exterior side of the atrial dome 151. Thereby restoration of the normal continuity between the papillary muscles 170 and left ventricular wall and the mitral valve 130 may be accomplished.

In either of the embodiments of the above described first aspect of a method according to the invention, the annuloplasty ring 10 may alternatively be entered through the mitral valve 130 from the atrium 150 to the ventricular cavity 110 and secured/fixated to the ventricular side 180b of the annulus 180 upon securing the second ends 21b, 22b, 23b, 24, 25b at their respective locations as described above. Consequently, the first ends 21a, 22a, 23a, 24a, 25a of the tension members must be brought through the annulus 180 prior to fixating the annuloplasty ring to the annulus. The first ends 21a, 22a, 23a, 24a, 25a of the tension members are then exteriorized through the dome 151 of the left atrium 150, adjusted and tied or tightened and anchored in a standard surgical fashion on the exterior side of the atrial dome 151, in the same manner as described above.

In a second aspect of a method for altering the geometry of a heart using the system 201, shown and described in relation to FIG. 4, the first ends 221a, 222a, 223a, 224a of the annulus-papillary tension members 221, 222, 223, 224 are brought from the atrial 180a to the ventricular 180b aspect of the annulus 180 by piercing the annulus 180 at positions corresponding to the points of departure of the tension members 221, 222, 223, 224 from the annuloplasty ring 210. Hereafter the annuloplasty ring 210 is fixated to the atrium side 180a of the annulus 180, e.g. by means of interrupted sutures following standard surgical techniques. The first ends 221a, 222a, 223a, 224a of the annulus-papillary tension members 221, 222, 223, 224 are passed through the papillary muscles 170 and left ventricular wall 111 from the papillary muscle tips 170a to the epicardial aspect 170b of the papillary muscle base, such that the first ends 221a, 222a, 223a, 224a are exteriorized at the epicardial aspect 170b of the papillary muscle bases (as a rule at two locations). The annulus-papillary tension members 221, 222, 223, 224 may be passed through a passage pierced through the papillary muscle 170, either from the ventricular side 170a of the papillary muscles 170, or from the epicardial aspect 170b of the papillary muscle bases on the exterior side of the ventricular wall 111. Alternatively, this passage may be equipped with a tubular anchor extending through the papillary muscle 170 forming an enforced channel.

The valve-papillary tension members 221, 222, 223, 224 are distributed such that each of a pair of tension members from each point of departure on the annuloplasty ring 210 are connected to different ones of the papillary muscle tips 170a.

At least one passage for each tension member is preferably formed through each papillary muscle 170, through which the tension member is passed. Alternatively, all the tension members through a papillary muscle 170 may be passed through a single passage formed in each papillary muscle 170.

Then the heart is surgically closed, its cavities evacuated from air and allowed to fill with blood, and normal heart rhythm resumed. Under echocardiographic guidance the tension members 221, 222, 223, 224 are adjusted (tightened or loosened relative to each other) to maximize cardiac function and valve competence. Hereafter the tension members 221, 222, 223, 224 are tied in a standard surgical fashion, or tightened in a standard surgical fashion around an anchor such as a special epicardial pad to reduce the local myocardial damage.

In another embodiment of this second aspect of a method according to the invention, using the system 1 shown and described in relation to FIG. 5 a further inter-papillary tension member 225 may be placed in the heart along with the valve-papillary tension members 221, 222, 223, 224. A ventricular end 225b of the inter-papillary tension member 225 is fixed to a tip 170a of one of the papillary muscles 170, either at a separate fixture or to a ventricle end of one tubular papillary anchor.

An inter-papillary anchor 32 is then fixed to a tip 170a of the other of the two papillary muscles 170 in connection with a passage pierced through the papillary muscle 170, either from the ventricular side 170a of the papillary muscles 170, or from the epicardial aspect 170b of the papillary muscle base on the exterior side of the ventricular wall. Then the first end 225a of the inter-papillary tension member 225 is exteriorized via the inter-papillary anchor 32 through the passage.

Upon closing and resuming the heart rhythm, the annulus-papillary tension members 221, 222, 223, 224 are then adjusted by manipulating the second ends 221b, 222b, 223b, 224b of the valve-papillary tension members 221, 222, 23, 224, (tightened or loosened relative to each other) to maximize cardiac function and valve competence. Hereafter the tension members 221, 222, 223, 224, 225 tightened in a standard surgical fashion around an anchor 230 such as a special epicardial pad to reduce the local myocardial damage on the exterior side of the epicardial aspect 170b of the papillary muscle base.

Thereby restoration of the normal continuity between the papillary muscles 170 and left ventricular wall and the mitral valve 130 may be accomplished.

In either of the embodiments of the above described second aspect of a method according to the invention the annuloplasty ring 10 may alternatively be entered through the mitral valve 130 from the atrium 150 to the ventricular cavity 110 and secured/fixated to the ventricular side 180b of the annulus 180, and the remainder of the method can be carried out as outlined above.

Similar methods may apply for the right atrium/ventricle and tricuspid valve, by adapting the system and methods to forming links between each of the three papillary muscles (corresponding to the three leaflets of the tricuspid valve) in the right ventricular chamber.

The tension members may be marked (texture) or color-coded texture in order to differentiate between the tension members, and thereby between the relevant anatomical lengths inside the beating heart to be adjusted. Markings/attachable signs could also be attached to the first ends 21a, 22a, 23a, 24a, 25a, during the surgical procedure as each tension member is exteriorized in order to differentiate between the tension members/anatomical lengths when the adjustment step is to take place.

Figure 7A:
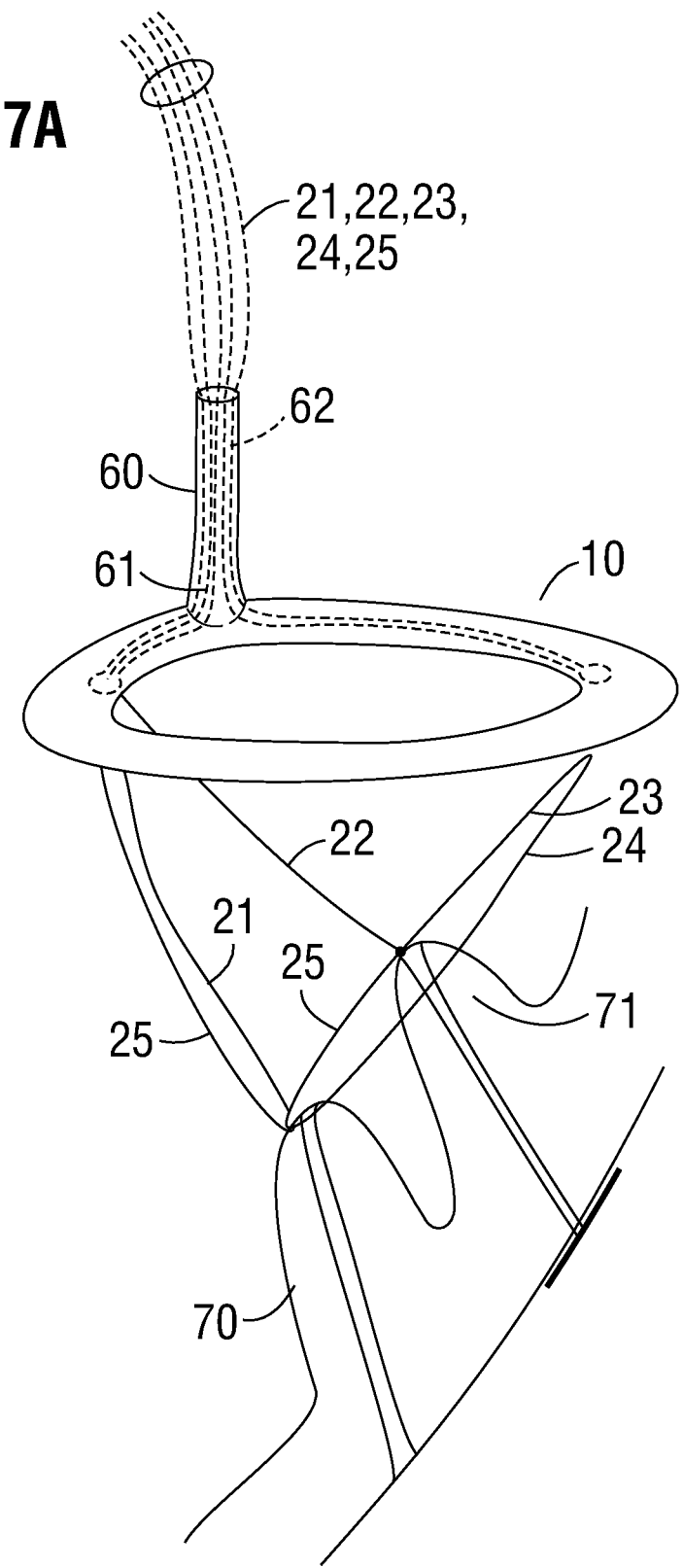
FIG. 7A shows a perspective view of a system for altering the geometry of a heart according to an embodiment of the first aspect of the invention.

In a further embodiment of the first aspect of the system 1 according to the invention, and with reference to FIGS. 7A and 7B, the annuloplasty ring 10 may be provided with an extension tubing 60 communicating with the internal compartment 14 of the ring 10 through the aperture 11 in upper side 10a of the ring 10. The extension tubing 60 is adapted to extend through the atrium 150 and through the atrium wall 151, and carries the first ends 21a-24a (or 25a) of said tension members 21-24 (or 25). The extension tubing 60 is provided with means disposed at the end 61 closest to the annuloplasty ring 10 for squeezing of and fixating the tension members by turning of the extension tubing 60 around the longitudinal axis thereof. Thereby, the tension member length can be adjusted from the external side of the atrium on the beating heart by turning an externally extended part 62 of the extension tubing 60, thus securing the tension members in the correct position. By further providing the extension tubing 60 with a cutting mechanism (not shown), e.g. by an internal flange having a cutting edge, activated by further squeezing of and cutting the tension members, said cutting edge being disposed above said fixation point in said extension tubing 60, and being actuated by a further turning action of the extension tubing 60; and by means for cutting off at least a section of the extension tubing 60 itself (e.g. by a weakening of the wall of the extension tubing 60 above the cutting flange for the tension members, by further turning action) a major part of the extension tubing 60 can be pulled out of the atrium 150, leaving the tension members anchored at the annuloplasty ring 10 inside the atrium. Thus a restoration of the geometry of the heart can be accomplished from the atrium side, leaving no anchors on the atrium wall, which is thinner than e.g. the ventricle wall. Thus the atrium wall can be further relieved of some stress over the long term.

Figure 8A:
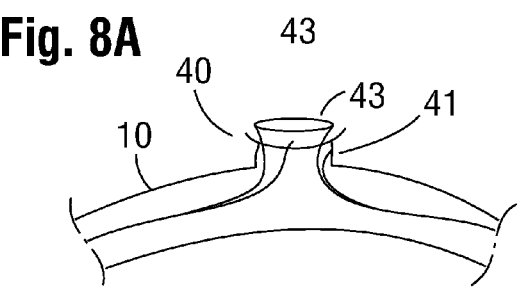
FIGS. 8A-D show details of yet another embodiment of a system for altering the geometry of a heart according to the first aspect of the invention.
Figure 8B:
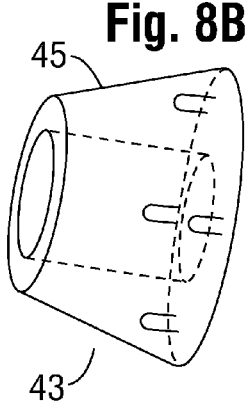
Figure 8C:
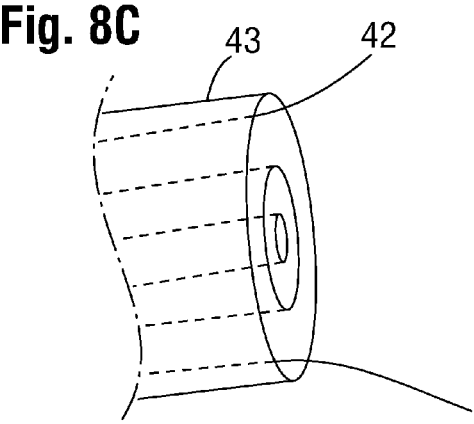
Figure 8D:
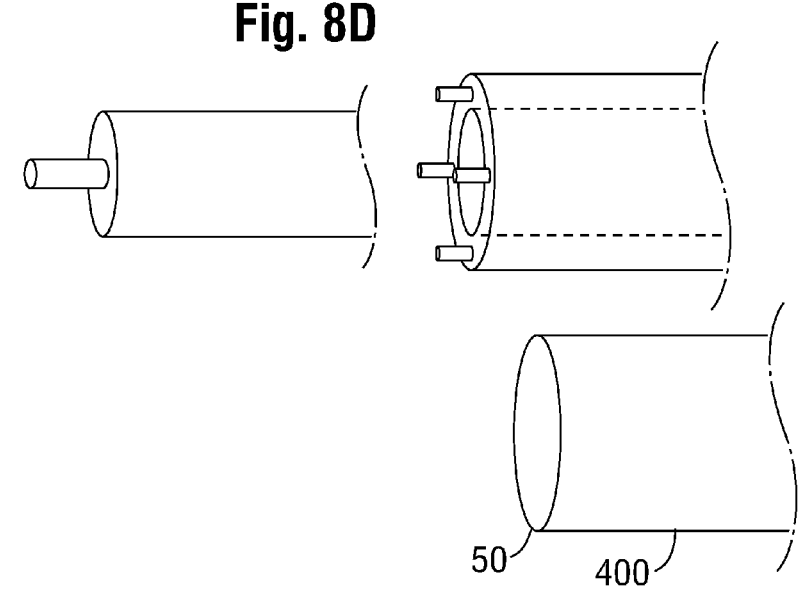
Figure 9:
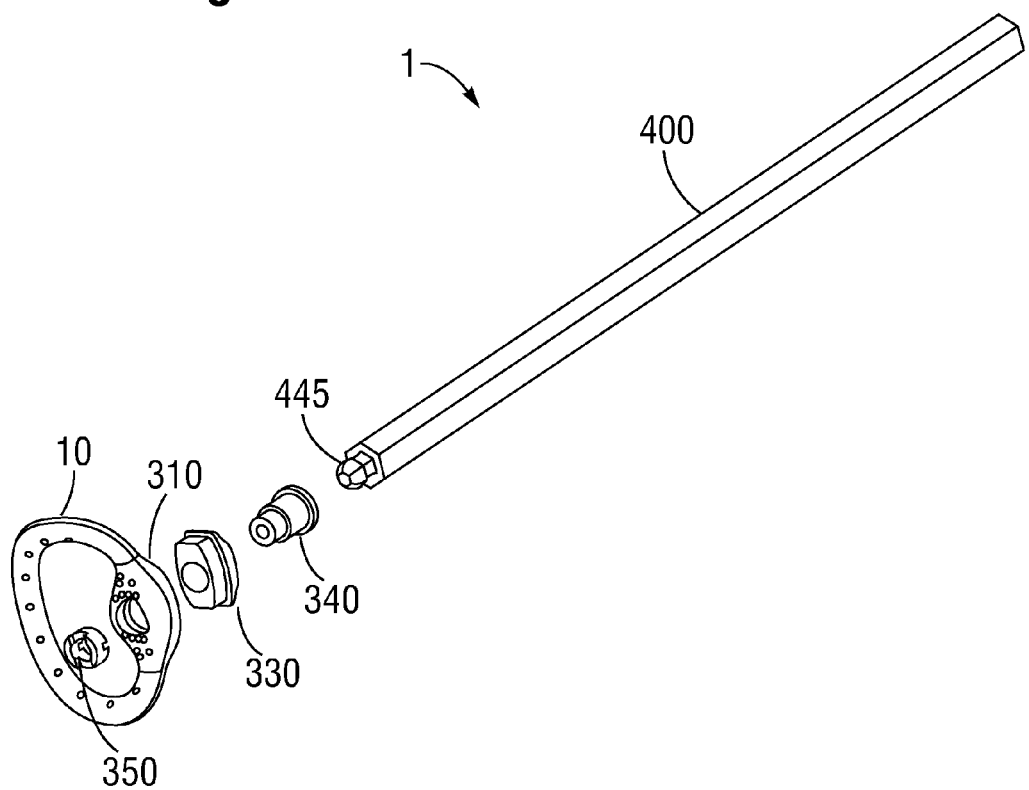
FIG. 9, in an exploded, perspective view, shows details of yet another embodiment of a system, including a tightening tool, for altering the geometry of a heart according to the first aspect of the invention; the system is shown from the lower side.
Figure 10:
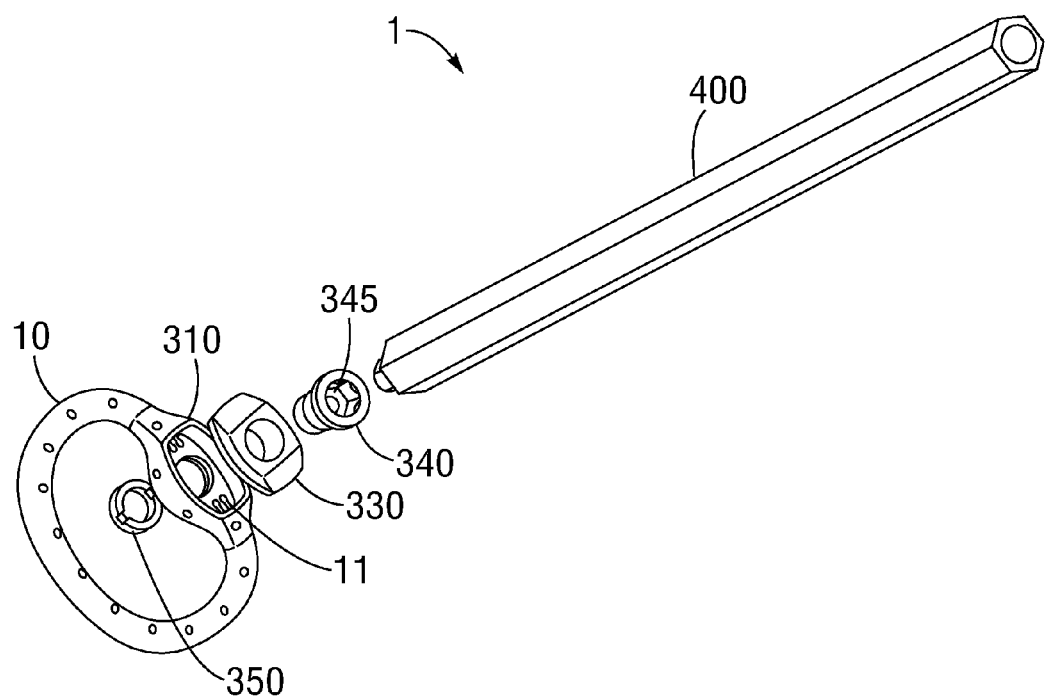
FIG. 10, in another exploded, perspective view, shows the system of FIG. 9; the system is seen from above.
Figure 11:
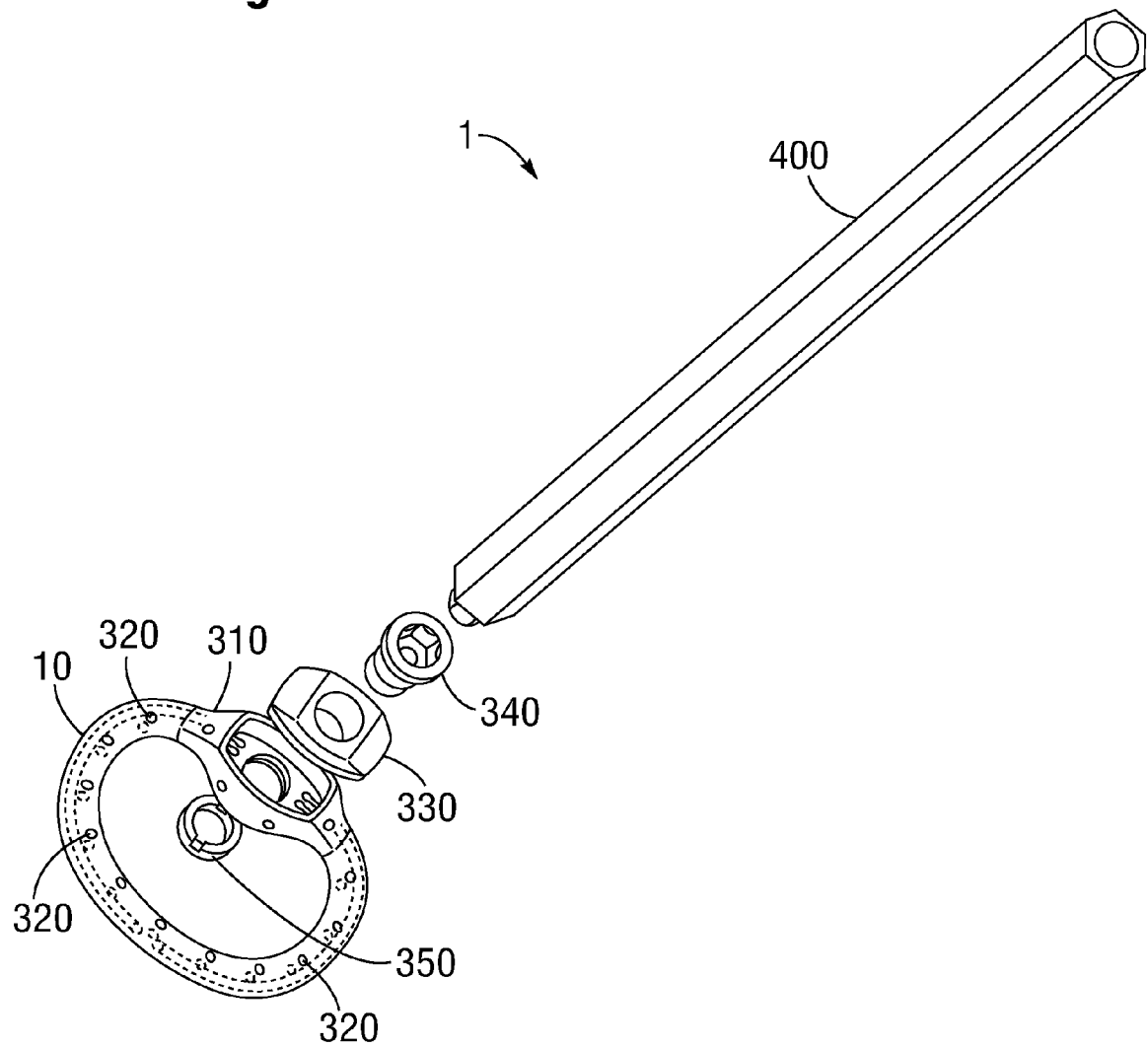
FIG. 11 shows an outline of the system in FIG. 10.
Figure 12:
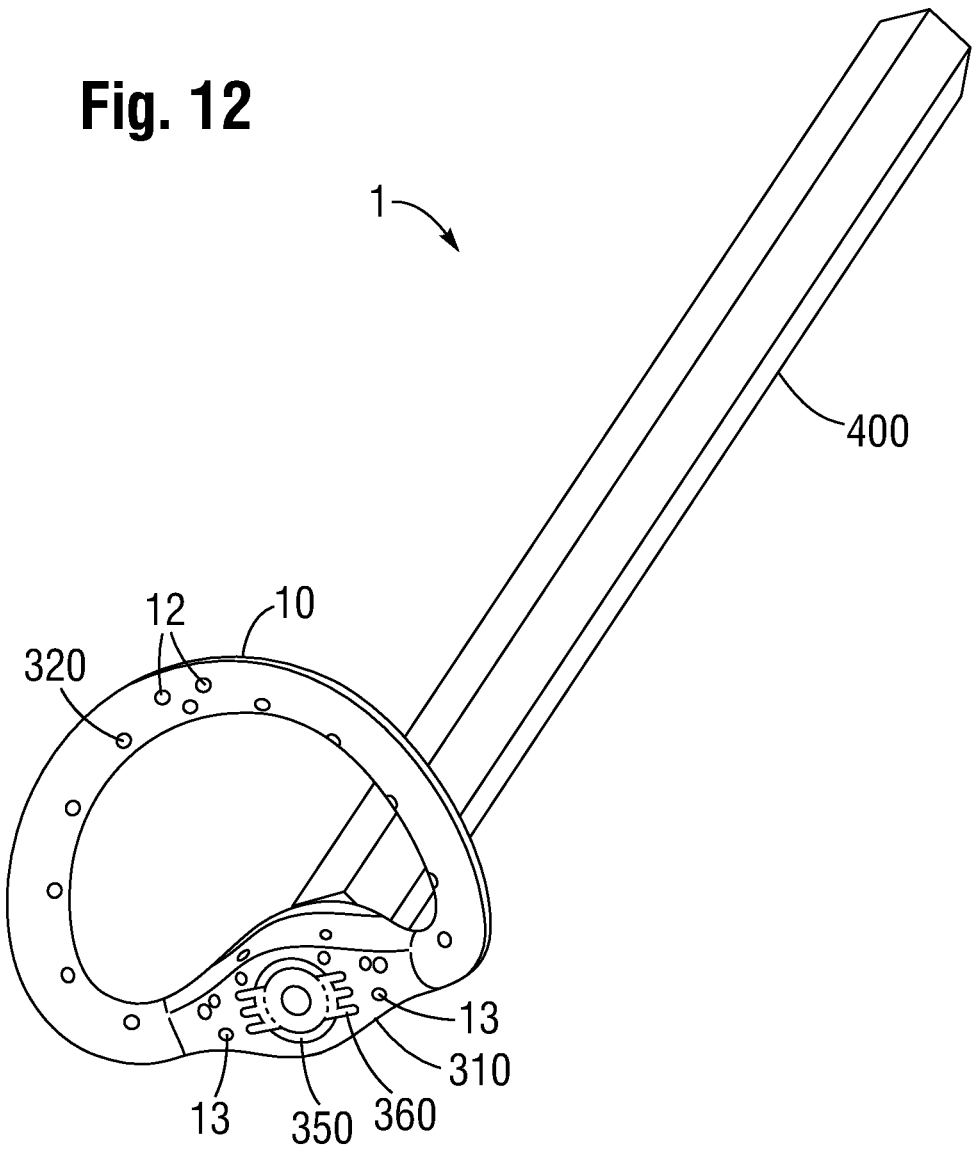
FIG. 12, in a perspective view, shows the system of FIGS. 9-11 in an assembled state, and with a tightening tool engaging an annuloplasty ring of the system.

In yet a further embodiment of the first aspect of the system 1 according to the invention, and with reference to FIG. 8A-D, the annuloplasty ring 10 may be provided with an alternative system 40 for fixating said tension members 21-24 (or 25) at said atrium/upper side 10a of said annuloplasty ring 10. In this embodiment the annuloplasty ring 10 is provided with a short upwardly directed tubular extension 41, communicating with the upper aperture 11. The tension members are extending through said tubular extension 41. In the tubular extension 41 a pin 45 having a threading is provided. The threading is adapted for cooperation with an internal threading of a plugging member 43 adapted to be received in said tubular extension 41. The tubular extension further has a cutting edge 42. The plug further has a conical outer surface for cooperation with said edge 42, and preferably a corresponding conical part in the upper part of the tubular extension 41 lumen. When the system 1 has been correctly inserted into the heart 100, the atrium has been closed (with the tension members extending therefrom), the heart rhythm has been reinstated and the heart has been correctly placed in the thorax, and the tension members has been adjusted to alter the geometry of the ventricle as desired, then the plugging member 43 can be turned using a suitable tool, e.g. as shown in FIG. 8D. By turning the plugging member 43 the plugging member is moved towards the annuloplasty ring 10 squeezing the corresponding conical surfaces on the tubular extension 41 and the plugging member 43 together, thus fixating the tension members. By a further turning the plugging member 43 the tension members are cut between the cutting edge 42 and the conical part of the plugging member 43.

Figure 13:
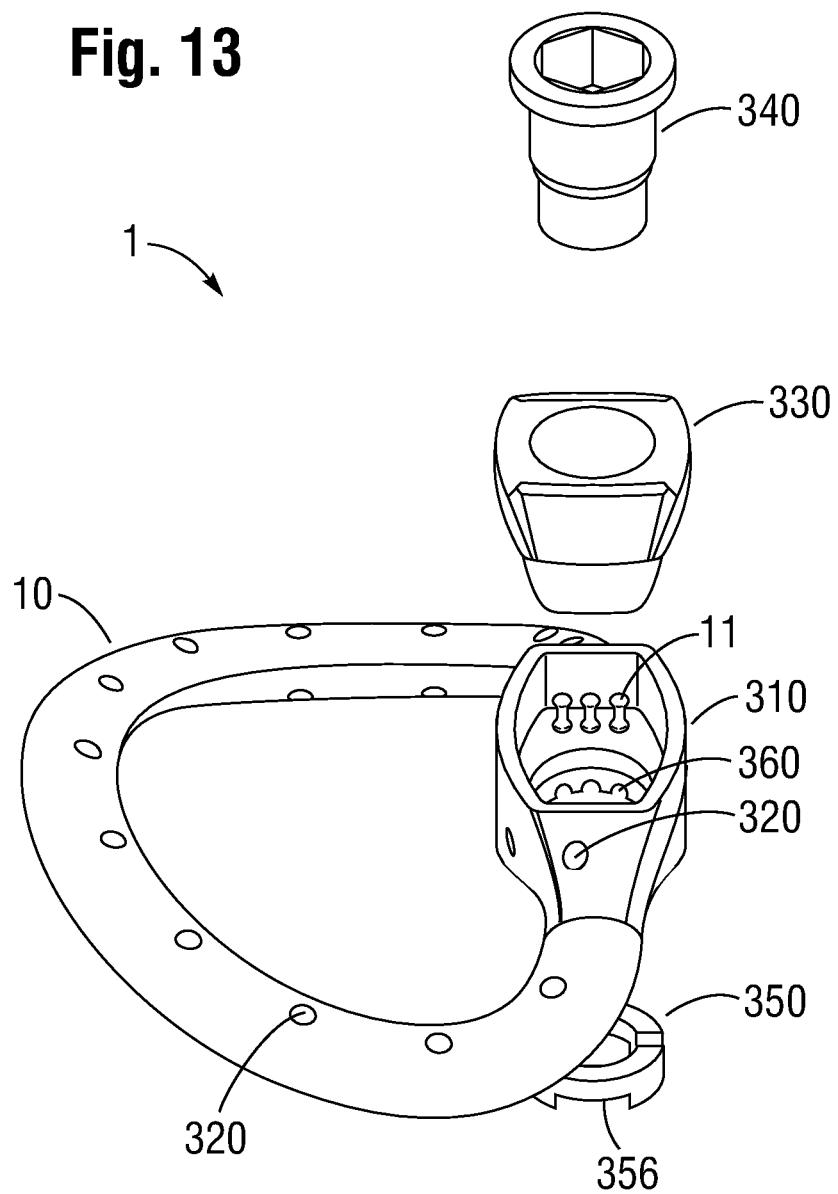
FIG. 13, in an exploded perspective view, shows details of an annuloplasty ring for a system as shown in FIGS. 9-13, as seen from above.
Figure 14:
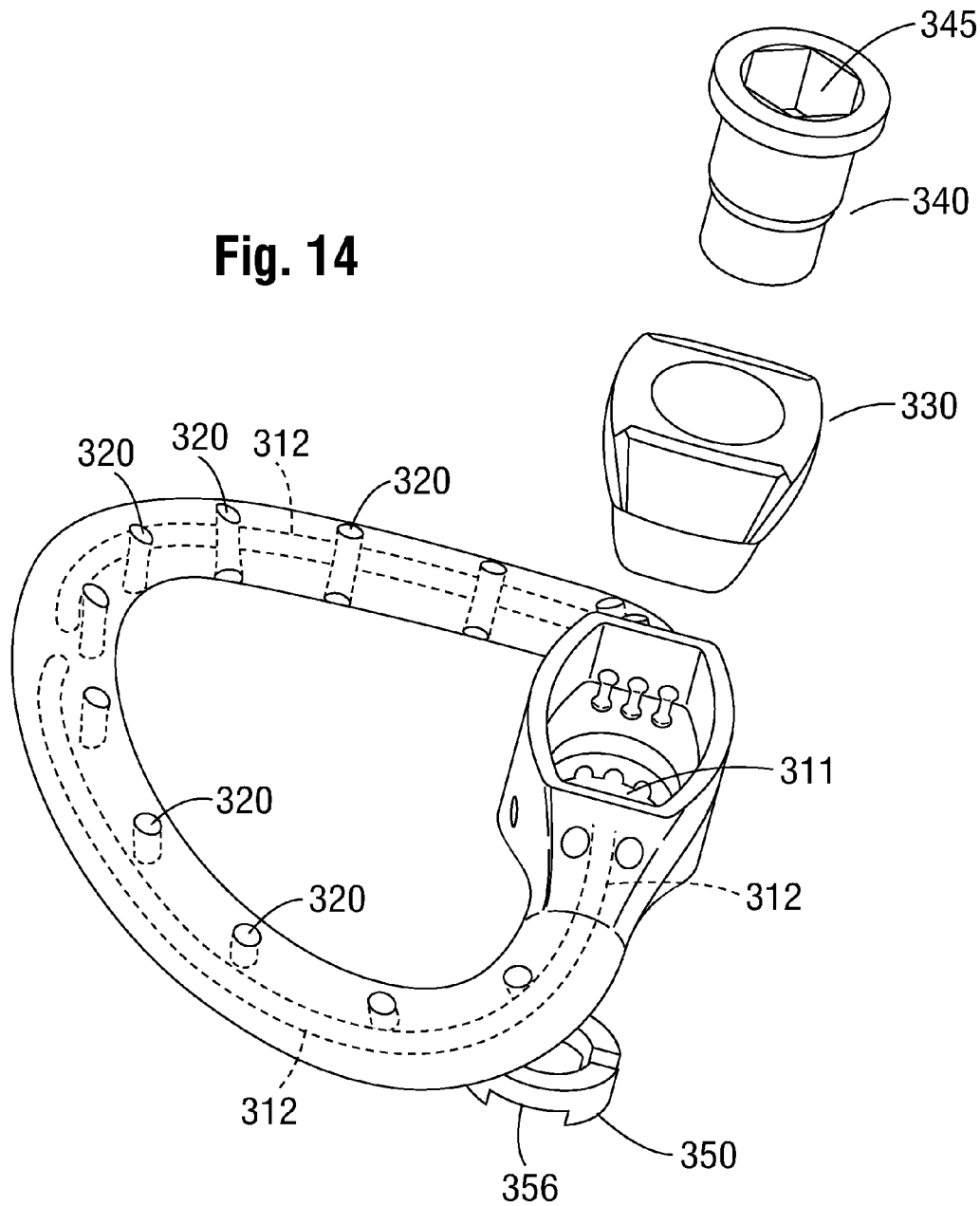
FIG. 14 shows an outline of the annuloplasty ring of FIG. 13.
Figure 15:
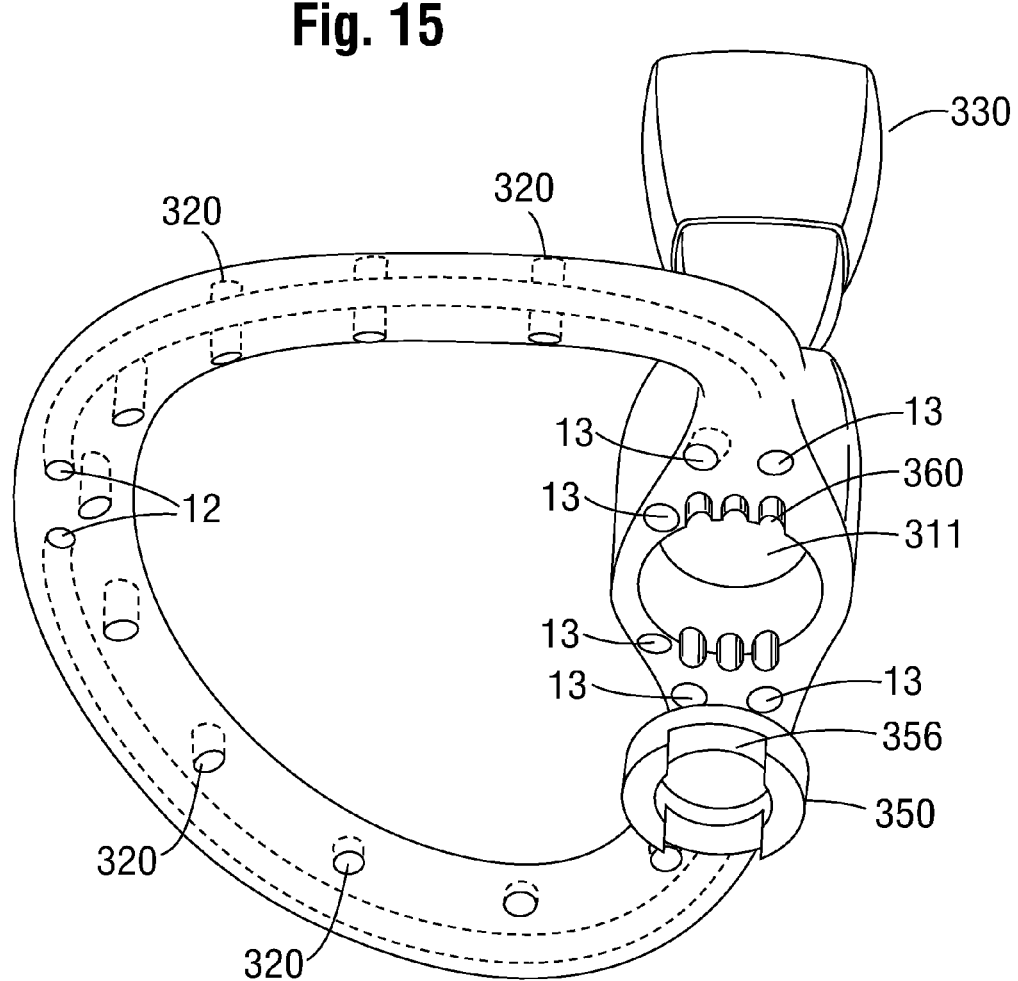
FIG. 15, in outline, shows the annuloplasty ring of FIG. 13, as seen from below.

In yet an embodiment of the first aspect of the system 1 according to the invention, and with reference to FIGS. 9-17, the annuloplasty ring 10 may be provided with an alternative system 40 for fixating said tension members 21-24 (and 25) at said atrium/upper side 10a of said annuloplasty ring 10. In this embodiment, the annuloplasty ring 10 has a tension member hub 310 through which the tension members 21-25 are extended, the hub 310 providing means for fixating the tension members 21-25 when the desired length/tension has been achieved. As shown in FIG. 13, in an exploded, perspective view the annuloplasty ring 10 may have a saddle shape with a hub 310 at one side. Thus, the shape of the annuloplasty ring 10 is adapted to the natural shape of the annulus 180. However, the annuloplasty ring 10 may in other embodiments be e.g. circular or oval-shaped, or have other 3-dimentional configurations in order to adapt the annuloplasty ring to aid the restoration/repair of the individual annulus and mitral valve dilation.

In FIG. 13, it is shown that the annuloplasty ring 10 comprises a set of additional attachment holes 320 extending through the ring 10 from the atrium, upper side 10a to the lower, ventricle side 10b. These additional attachment holes 320 are provided as a means of sewing/stitching/suturing the ring 10 to the annulus 180 of the heart. However, other means for attachment/fixating the annuloplasty ring 10 to the annulus may be provided as alternative or as additional to the attachment holes 320. The annuloplasty ring 10 may e.g. be provided with a web of material on the outer surface of the ring 10, as known in the art, providing an anchoring for the suturing the ring 10 to the annulus.

The hub 310 of the annuloplasty ring 10 comprises a through hole 311 in which a locking part 330 for locking/fixating the tension members 21-25 is mountable, the locking part 330 also having a through hole 331. The hub 310 further comprises fastening means 340, 350 for locking/fixating the locking member to the though hole 311 of the hub 310. As will be described in further detail below, the fastening member 340 may be tightened by a specially adapted hollow tightening tool 400. In the embodiment shown in FIGS. 9-16 the fastening means 340, 350 are a bolt 340 (having a through hole 341) and a nut 350 (having a through hole 351), and the tightening tool 400 has an Allen key type means 445 of engaging the fastening means (the bolt 340), the fastening means 340 having cooperating engagement means 345. However, other embodiments of these features may be utilized. For example the nut 350 may be replaced by a threading provided within at least a section of the hub 310 through hole 311.

The fastening part 340 (the bolt) extends through the through hole 331 in the locking part 330 and the through hole 311 in the hub 310. The fastening part 340 has a threading cooperating with a threading on the lower fastening part 350 (the nut). The lower fastening part 350 is received in and prevented from rotation with respect to the hub 310. The locking member 330 is received in the through hole 311 of hub 310 such that it is prevented from rotation, preferably by corresponding parts of the locking part 320 and the through hole 311 being non circular.

The annuloplasty ring 10 has a set of apertures 11 provided in the upper/atrium side 10a, for accommodating the tension members 21-25 extending from the atrium of the heart. The apertures 11 on the upper side 10a communicate with a set of apertures 12, 13 on the lower (ventricle) side 10b of the annuloplasty ring 10, from/to where a set of tension members 21-25 can be extended to be fixed to regions of the ventricle of a heart (when inserted into the heart of a human or animal). As seen in the FIGS. 13-16 all the apertures 11 on the upper side 10a are located at the hub 310 in order to provide an easy way of adjusting and fixating the tension members from a position outside the heart and through the atrium. Some of the communicating apertures 11, 13 communicate via channels 313 through the annuloplasty ring 10 that are located in the vicinity of the hub 310, such that the lower side 10b apertures 13 are located on or right next to the lower side of the hub 310. Other of the communicating apertures 11, 12 communicate via channels 312 through the annuloplasty ring 10 that extend from the upper side 10a apertures 11 to the lower side 10b apertures on positions arranged distributed over the lower surface 10b of the ring 10. As shown, in the FIGS. 13-16 these lower side 10b apertures 12 are preferably located at positions diametrically opposite the hub 310 in order to provide an optimal distribution of the tension members 21-25, to allow the best possible adjustment to restore or improve the geometry of the ventricle.

The channel(s) 312 extending from the upper apertures 11 at the hub to the diametrically opposed lower side 10b apertures 12 may extend completely within the annuloplasty ring 10 as closed channels. However, in other embodiments, at least part of the channel(s) 312 may be provided as open grooves (e.g. C-shaped in cross section) in the outer perimeter of the annuloplasty ring 10. A (partly) open channel may allow for easier placement/mounting of the tension members 21-25 at manufacture or on site prior to the insertion of the annuloplasty ring/system for altering the geometry of the heart.

Figure 16:
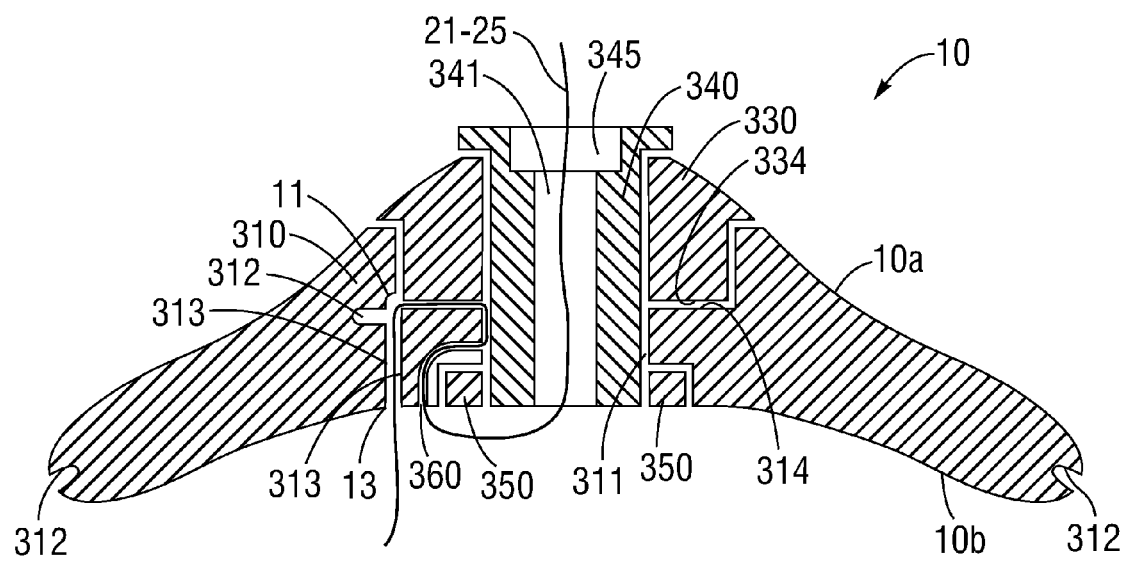
FIG. 16 shows a section through a hub part of an annuloplasty ring as shown in FIGS. 13-15.

A (partly) open channel 312 is illustrated in FIG. 16, which shows a sectional view through an annuloplasty ring 10, the locking part 330, the fastening parts 340,350 (bolt and nut) being screwed into the ring 10, and a tension member 21-25 being shown to indicate how the tension members are carried for fixation. In FIG. 16, the space between the individual components has been exaggerated in order to allow illustration of the path of a tension member 21-25 through the annuloplasty ring 10. The channel 312 begins at the aperture 11 and extends through the hub 310 to the outer perimeter of the ring 10 proper as a closed channel, then around the outermost part of the ring perimeter as an open channel. However, as indicated above, the channels 312 may in other embodiments be closed through its entirety from upper apertures 11 to lower apertures 12.

FIG. 16, as mentioned, also illustrates the path of a tension member 21-25 through the annuloplasty ring 10, as could be the situation when the ring 10 is fixed to the annulus, the tension members 21-25 being adjusted and fixed. The tension member 21-25 extends from the atrium side (up in the figure) down through a through hole 341 in the fastening member 340. Then the tension member 21-25 extends back up between the outer surface of the fastening member 340 and surface of the through hole 311 of the hub 310 and on between a flange 314 of the through hole 311 of the hub 310 and a lower surface 334 of the locking part 330. Here the tension member enters the hub 310 of the ring 10 through upper aperture 11 in the ring 10. The tension member is shown extending through a channel 313 in the vicinity of the hub 310 to aperture 13 and through the tissue surrounding the annulus and into the ventricle. Another tension member 21-25 (not shown in FIG. 16) would extend into channel 312 and to a position opposite the hub 310 or on another location on the circle of the annuloplasty ring lower side 10b.

The tension member is fixated in the desired position by screwing the upper fastening part 340 (the bolt) in such that the tension member is locked or squeezed between the surfaces 314, 334 on the hub 310 and locking part 330, respectively. Thus, it is avoided that the tension member is rotated and/or ruptured during the screwing in of the fastening member. Further, in order to avoid contact between the tension members and the lower fastening part 350 a set of grooves 360 is provided on the lower side of the hub 310. Further, a set of grooves 356 are provided on the lower surface of the lower fastening part 350. Thus the tension members can be freely adjusted until there is formed a contact between the surfaces 314, 334 on the hub 310 and locking part 330, respectively.

The annuloplasty ring 10 is inserted into the heart through the atrium, as is the case with the other embodiments and aspects described above. The annuloplasty ring 10 is fixed to the annulus by means of suturing the ring 10 via the attachment holes 320 (or by any of the other means described), as is the case with the other embodiments and aspects described above. The pre-installed tension members 21-25 are, or have been, extended into the ventricle through the tissue of the annulus and secured to the respective desired points in the ventricle (papillary muscles or other points on the inner ventricle wall), or they may be anchored through the papillary muscles, as described above. The opening through the atrium wall through which the annuloplasty ring/system was entered is then partly closed, the tension members passed through the remaining opening. The heart is weaned from cardiopulmonary bypass, such that it is beating. Then the tension members are adjusted such that the original geometry of the heart (or at least the ventricle) is obtained, or at least partly regained. Then the tension members are locked or fixated in the desired position (state of tension) obtained by the adjustment by turning of the fastening member 340 by a tightening tool 400 engaging the fastening member 340.

The tightening tool 400 is hollow, i.e. it has an elongate bore 401, extending through the length of the tool 400, as can be appreciated from FIG. 17, showing an elongate section through the tool 400. Thus the tension members 21-25 can be contained within the bore 401 when the locking occurs (by turning of the tightening tool 400 engaging the upper fastening part 340 (the bolt)), and when the adjustment of the tension member lengths in the ventricle takes place.

When the tension members has been locked/fixated to the annuloplasty ring 10, the part of the tension members situated in the atrium may be cut at the ring 10, the tightening tool 400 is retracted and the remaining opening in the atrium wall is closed. Otherwise the tension members 21-25 may be left extending from the ring 10 to the opening in the atrium, the tightening tool 400 is retracted and the remaining opening in the atrium wall is closed, and the tension members secured to the outer wall of the atrium.

When the ring 10 has been attached to the annulus and the tension members has been secured/anchored in the ventricle the atrium end of the tension members are preferably passed through the elongate bore or cavity in the tightening tool entered through the opening in the atrium, such that the adjustment of and the tightening/locking of the tension members can be carried out using the tightening tool. The tightening tool therefore is adapted in length to be able to reach to the annulus of a heart from the outside of the atrium of a heart. As described above, when the tension members are passed through the tightening tool and prior to the weaning of the heart and the adjustment of the tension members, the opening in the atrium must be partly closed, in order to allow access to the annuloplasty ring (with the tightening tool) and at the same time prevent blood flow from the opening. This is preferably done by providing the opening with a purse string suture.

Prior to the procedure of implanting a system according to any of the aspects of the invention described a scanning, e.g. an MR scanning of the heart may be performed in order to prepare the procedure and possibly make adjustments to the system in general or the annuloplasty ring in particular.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A method for adjusting, from outside the heart and while the heart is beating, the distance between a native heart valve annulus and associated papillary muscles located within the adjacent ventricle, comprising:

stopping the heart of the patient from beating;
resecting the heart wall of one of the atriums;

inserting a system for altering the geometry of a heart into the atrium, the system comprising a substantially rigid annuloplasty ring having an upper side and a lower side, an upper aperture located on the upper side and at least two lower apertures located on the lower side that are spaced apart from each other and at least one being spaced from the upper aperture around the annuloplasty ring, the annuloplasty ring further including channels that extend between the upper aperture and each of the lower apertures, the system further including at least two flexible, elongate annulus-papillary tension members that each extend from a second end through one of the lower apertures in the annuloplasty ring, through one of the channels, and through the upper aperture to a first end;

passing the second ends of the tension members into the ventricle associated with the atrium;

attaching each of the second ends of the tension members to a papillary muscle;

attaching the annuloplasty ring to the heart valve annulus between the atrium and the associated ventricle;

extending the first ends of the tension members from the upper aperture of the annuloplasty ring to a position outside the atrium; and after restarting the heart of the patient and while the heart is beating, adjusting the distance between the second ends of the tension members and the annuloplasty ring by manipulating the first ends of the tension members from outside the atrium.

2. The method of claim 1, wherein the step of passing the second ends of the tension members into the ventricle includes passing the second ends of the tension members through the tissue of the annulus.

3. The method of claim 1, wherein the annuloplasty ring further includes a tension member hub open to the upper side of the annuloplasty ring, the hub defining the upper aperture and further including a locking part that engages the hub and is adapted for locking the position of the tension members through the upper aperture, and the method includes operating the locking part to lock the position of the tension members through the upper aperture.

4. The method of claim 3, wherein the system includes a fastening member for tightening the locking part against the tension member hub, and a tightening tool that engages the fastening member and has a length sufficient to extend from the annuloplasty ring through the atrium to a position outside the atrium for manipulation thereof, and the method includes engaging the fastening member with the tightening tool so as to tighten the locking part against the tension member hub.

5. The method of claim 4, wherein the tightening tool is hollow, and the tension members extend from the upper aperture through the tightening tool.

6. The method of claim 1, further including locking the position of the tension members through the upper aperture, cutting the tension members at the annuloplasty ring, and removing from the atrium portions of the tension members between where they were cut to their first ends.

7. The method of claim 1, further including locking the position of the tension members through the upper aperture and securing the tension members to the outer wall of the atrium.

8. A method for adjusting, from outside the heart and while the heart is beating, the distance between a native heart valve annulus and associated papillary muscles located within the adjacent ventricle, comprising:

stopping the heart of the patient from beating;
resecting the heart wall one of the atriums;
inserting a system for altering the geometry of a heart into the atrium, the system comprising a substantially rigid annuloplasty ring having an upper side and a lower side, an upper aperture located on the upper side and a lower aperture located on the lower side and spaced from the upper aperture around the annuloplasty ring, the annuloplasty ring further including channels that extend between the upper aperture and the lower aperture, the system further including a flexible, elongate annulus-papillary tension member that extends from a second end through the lower aperture in the annuloplasty ring, through one of the channels, and through the upper aperture to a first end;

passing the second end of the tension member into the ventricle associated with the atrium;

attaching the second end of the tension member to a papillary muscle;

attaching the annuloplasty ring to the heart valve annulus between the atrium and the associated ventricle;

extending a tool from outside the atrium through an opening in the wall of the atrium to the upper aperture;

sealing the opening in the wall of the atrium around the tool;

restarting the heart of the patient;

after restarting the heart of the patient and while the heart is beating, adjusting the distance between the second end of the tension member and the annuloplasty ring by manipulating the first end of the tension member; and locking the position of the tension member through the upper aperture using the tool.

9. The method of claim 8, wherein the annuloplasty ring further includes a tension member hub open to the upper side of the annuloplasty ring, the hub defining the upper aperture and further including a locking part that engages the hub and is adapted for locking the position of the tension member through the upper aperture, and the method includes operating the locking part to lock the position of the tension member through the upper aperture.

10. The method of claim 9, wherein the system includes a fastening member for tightening the locking part against the tension member hub, and the tool engages the fastening member and has a length sufficient to extend from the annuloplasty ring through the atrium to a position outside the atrium for manipulation thereof, and the method includes engaging the fastening member with the tool so as to tighten the locking part against the tension member hub.

11. The method of claim 8, wherein the tool is hollow, and the first end of the tension member extends through the tool to a position outside the atrium.

12. The method of claim 8, further including locking the position of the tension member through the upper aperture, cutting the tension member at the annuloplasty ring, and removing from the atrium a portion of the tension member between where it was cut to its first end.

13. The method of claim 8, further including locking the position of the tension member through the upper aperture and securing the tension member to the outer wall of the atrium.

14. The method of claim 8, wherein the annuloplasty ring has two of the lower apertures located on the lower side that are spaced apart from each other, at least one being spaced from the upper aperture around the annuloplasty ring, and wherein there are two of the channels extending between the upper aperture and each of the two lower apertures, the system further including two of the flexible, elongate annulus-papillary tension members, and each tension member extends from a respective second end through one of the lower apertures in the annuloplasty ring, through one of the channels, and through the upper aperture to a respective first end, the method including:

after restarting the heart of the patient and while the heart is beating, adjusting the distance between the second ends of the two tension members and the annuloplasty ring by manipulating the first ends of the tension member; and locking the positions of the two tension members through the upper aperture using the tool.

15. A method for adjusting, from outside the heart and while the heart is beating, the distance between a native heart valve annulus and associated papillary muscles located within the adjacent ventricle, comprising:

stopping the heart of the patient from beating;

resecting the heart wall one of the atriums;

inserting a system for altering the geometry of a heart into the atrium, the system comprising a substantially rigid annuloplasty ring having an upper side and a lower side, an upper aperture located on the upper side and a lower aperture located on the lower side and spaced from the upper aperture around the annuloplasty ring, the annuloplasty ring further including channels that extend between the upper aperture and the lower aperture, the system further including a flexible, elongate annulus-papillary tension member that extends from a second end through the lower aperture in the annuloplasty ring, through one of the channels, and through the upper aperture to a first end;

passing the second end of the tension member into the ventricle associated with the atrium;

attaching the second end of the tension member to a papillary muscle;

attaching the annuloplasty ring to the heart valve annulus between the atrium and the associated ventricle;

extending the first end of the tension member from the upper aperture of the annuloplasty ring to a position outside the atrium;

sealing the opening in the wall of the atrium around the tension member;

restarting the heart of the patient;

after restarting the heart of the patient and while the heart is beating, monitoring cardiac function and valve competence while adjusting the distance between the second end of the tension member and the annuloplasty ring by manipulating the first end of the tension member; and locking the position of the tension member through the upper aperture.

16. The method of claim 15, wherein the annuloplasty ring further includes a tension member hub open to the upper side of the annuloplasty ring, the hub defining the upper aperture and further including a locking part that engages the hub and is adapted for locking the position of the tension member through the upper aperture, and the method includes operating the locking part to lock the position of the tension member through the upper aperture.

17. The method of claim 16, wherein the system includes a fastening member for tightening the locking part against the tension member hub, and a tightening tool that engages the fastening member and has a length sufficient to extend from the annuloplasty ring through the atrium to a position outside the atrium for manipulation thereof, and the method includes engaging the fastening member with the tool so as to tighten the locking part against the tension member hub.

18. The method of claim 17, wherein the tool is hollow, and the first end of the tension member extends through the tool to a position outside the atrium.

19. The method of claim 15, further including locking the position of the tension member through the upper aperture, cutting the tension member at the annuloplasty ring, and removing from the atrium a portion of the tension member between where it was cut to its first end.

20. The method of claim 15, further including locking the position of the tension member through the upper aperture and securing the tension member to the outer wall of the atrium.

21. The method of claim 15, wherein the annuloplasty ring has two of the lower apertures located on the lower side that are spaced apart from each other, at least one being spaced from the upper aperture around the annuloplasty ring, and wherein there are two of the channels extending between the upper aperture and each of the two lower apertures, the system further including two of the flexible, elongate annulus-papillary tension members, and each tension member extends from a respective second end through one of the lower apertures in the annuloplasty ring, through one of the channels, and through the upper aperture to a respective first end, the method including:

after restarting the heart of the patient and while the heart is beating, adjusting the distance between the second ends of the two tension members and the annuloplasty ring by manipulating the first ends of the tension member; and locking the positions of the two tension members through the upper aperture using the tool.

* * * * *